(12) United States Patent
Ronchi et al.

(10) Patent No.: US 8,167,799 B2
(45) Date of Patent: May 1, 2012

(54) APPARATUS AND METHOD FOR MONITORING STRAIN AND/OR LOAD APPLIED TO A MAMMAL

(76) Inventors: Andrew J Ronchi, Malvern East (AU); Daniel M Ronchi, Malvern East (AU)

( * ) Notice: Subject to any disclaimer, the term of this patent is extended or adjusted under 35 U.S.C. 154(b) by 1148 days.

(21) Appl. No.: 11/569,562

(22) PCT Filed: May 25, 2005

(86) PCT No.: PCT/AU2005/000743
§ 371 (c)(1),
(2), (4) Date: Dec. 7, 2007

(87) PCT Pub. No.: WO2005/115228
PCT Pub. Date: Dec. 8, 2005

(65) Prior Publication Data
US 2008/0221398 A1  Sep. 11, 2008

(30) Foreign Application Priority Data
May 25, 2004  (AU) ................ 2004902785

(51) Int. Cl.
*A61B 5/00* (2006.01)
*A61B 5/04* (2006.01)
*A61B 5/117* (2006.01)
*A61B 5/103* (2006.01)

(52) U.S. Cl. .................. 600/301; 600/546; 600/595

(58) Field of Classification Search ............. 600/587, 600/595, 546
See application file for complete search history.

(56) References Cited

U.S. PATENT DOCUMENTS

| | | | |
|---|---|---|---|
| 5,694,939 | A | 12/1997 | Cowings |
| 5,964,719 | A | 10/1999 | Costello et al. |
| 6,480,735 | B2 | 11/2002 | Colloca |
| 6,678,549 | B2 | 1/2004 | Cusimano et al. |
| 7,402,142 | B2 | 7/2008 | Kawai et al. |
| 2005/0080463 | A1 | 4/2005 | Stahmann et al. |

FOREIGN PATENT DOCUMENTS

| | | |
|---|---|---|
| JP | 9264810 A | 10/1997 |
| JP | 11-056801 A | 3/1999 |
| JP | 2001325362 A | 11/2001 |
| JP | 2004114288 A | 4/2004 |
| WO | 02/076293 A1 | 10/2002 |

*Primary Examiner* — Brian Szmal
(74) *Attorney, Agent, or Firm* — Lowe Hauptman Ham & Berner LLP

(57) ABSTRACT

Apparatus is disclosed for monitoring strain and/or load applied to the body of a vertebral mammal. The apparatus includes means (10, 11) for measuring position of the body relative to an inertial frame of reference and for providing first data indicative of the position, wherein the means for measuring position includes at least one inertial sensor such as an accelerometer. The apparatus includes means (12, 15-19) for measuring muscle activity and for providing second data indicative of the muscle activity. The apparatus also includes means for storing the data and means for processing the data to provide a measure of strain and/or load to the body. The strain and/or load is typically applied to the back of the mammal. A method of monitoring strain and/or load applied to the body of the vertebral mammal is also disclosed.

38 Claims, 36 Drawing Sheets

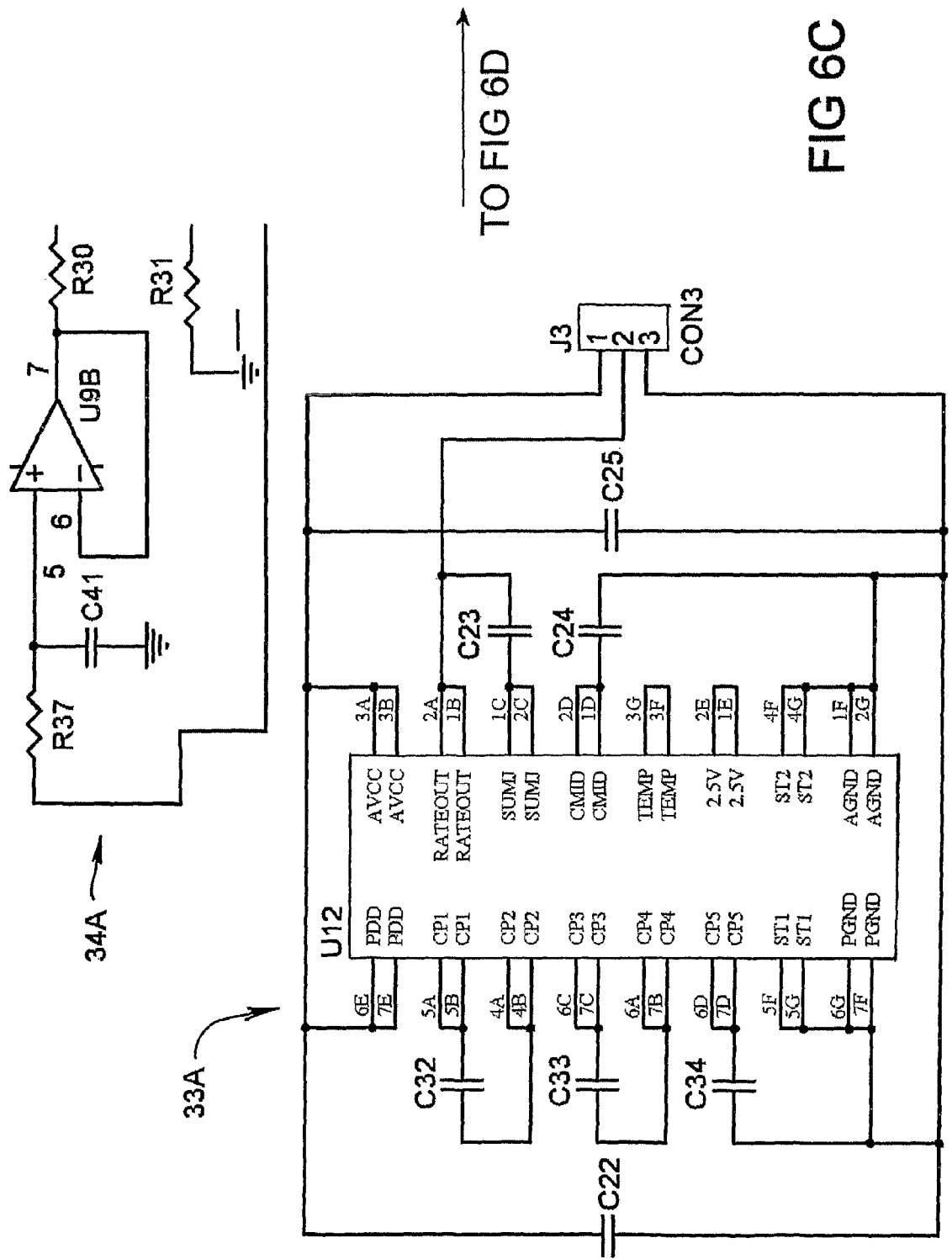

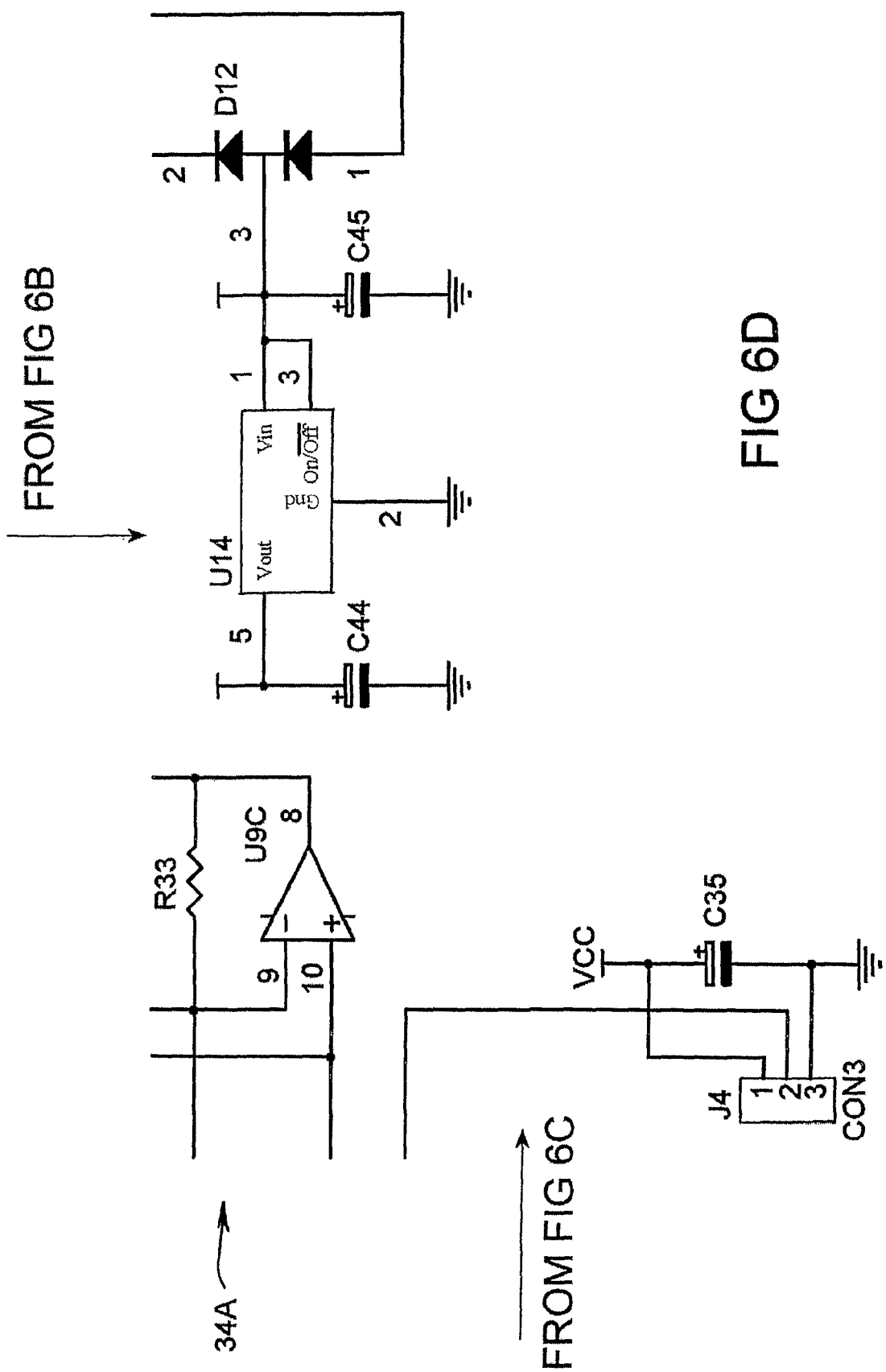

FIG 18A

Back Pain Questionnaire
Thankyou for completing this questionnaire.

Privacy: As you can see below, in the survey proper there is no identifiable information given during the survey, so please feel free to be as honest as you can.

However, if you feel comfortable leaving your name and contact phone number to allow the PhD student involved in this survey to contact you regarding the information you have provided in the survey if necessary, please do so below.

Please note, leaving your name and contact number is optional. Name: _____ Phone Number: _____

If contacted, it will be in relation to this study only.

Survey Aim: The research ultimately aims at providing better solutions to easing the pain of back injury and assisting with prevention of injury.

This particular survey is aimed at establishing relationships between personal attributes of people and susceptibility to back injury.

Survey Scope: This research is looking only at lower back injuries, specifically disc bulges, and how we may be able to prevent them.

If you have had injuries in areas of the spine/back, other than the lower back, they should not be considered when completing this questionnaire.

If you have suffered from an injury to the lower back that has required you to take 4 or more weeks off work, then the survey should be completed as if it were just before the injury occurred.

The occupation and Industry codes are used for questions on the following page.

| | Industry Classification |
|---|---|
| 0 | Agriculture, Forestry and Fishing |
| 1 | Mining |
| 2 | Manufacturing |
| 3 | Gas and Water Supply |
| 4 | Construction |
| 5 | Wholesale /Retail Trade (including Accommodation/Cafes & Restaurants) |
| 6 | Transport & Storage |
| 7 | Communications / Services (including Finance, insurance, property & business services) |
| 8 | Government Administration and Defence (including Education, Health & Community Services) |
| 9 | Cultural & Recreational Services (including Personal services) |

| | Occupation Classification |
|---|---|
| 1. | Managers and Administrators |
| 2. | Professionals |
| 3. | Associate Professionals |
| 4. | Tradespersons and Related Workers |
| 5. | Advanced Clerical and Service Workers |
| 6. | Intermediate Clerical, Sales and Service Workers |
| 7. | Intermediate Production and Transport Workers |
| 8. | Elementary Clerical, Sales and Service Workers |
| 9. | Labourers or Related Workers |

At each question, please enter either a specific figure, or tick a response grade that most applies to you.

1. Previous Personal Lumbar Injury (in weeks off work)
   Have you ever suffered a lower back injury which prevented you from performing your normal duties?

☐ N/A    ☐ Injury but no time off work    ☐ <2 weeks    ☐ 2 – 4 weeks    ☐ >4 weeks

IMPORTANT

If you ticked any of these boxes
   Please indicated the year of your initial injury
   and please complete the rest of the survey
   as if it were now a month before your initial injury.
   eg. If the injury occurred October 1998, fill in the application
   as though it were now September 1998.

2. Sex    ☐ Male    ☐ Female

3. Age    [ ] years

4. Height    [ ] millimetres

5. Weight    [ ] kilograms

6. Family History of Back Injury
   Have any of your parents suffered from lower back pain?

☐ None    ☐ 1 parent, mild    ☐ 1 pt, severe    ☐ 2 pt, mild    ☐ 2 pt, severe

7. Fitness
   How would you grade your overall fitness level?

☐ Very Unfit    ☐ Below Average Fitness    ☐ Average Fitness    ☐ High Level Fitness    ☐ Very High Fitness 8. Weight Lifted per day (kg)
   Estimate the total weight you would lift in a day.

| # | Question | | | | |
|---|---|---|---|---|---|
| 9. | Maximum Weight Per Lift. Estimate the weight of the heaviest lift you perform daily. | ☐ <5 | ☐ 5-10 | ☐ 11-20 | ☐ 21-40 | ☐ >40 |
| 10. | Hours Worked in a day Whether at home or at a workplace, estimate how many hours you work in a day on average. | ☐ <6 | ☐ 6-8 | ☐ 9-11 | ☐ 12-14 | ☐ >14 |
| 11. | Time per day lying down or sleeping How many hours a day do you spend resting? | ☐ >13 | ☐ 11-13 | ☐ 8-10 | ☐ 5-7 | ☐ <5 |
| 12. | Knee Pain Do you suffered from knee pain either currently, or knee pain that re-occurs periodically? | ☐ N/A | ☐ One Minor | ☐ One Major | ☐ 2 Minor | ☐ 2 Major |
| 13. | Occupation See Page 1 for codes. | See first page for codes | | | | |
| 14. | Industry See page 1 for codes. | See first page for codes | | | | |
| 15. | Time Per Day Spent Sitting (hours) How many hours per day do you spend sitting, either at work or at home? | ☐ <1 | ☐ 1-6 | ☐ 7-11 | ☐ 12-16 | ☐ >16 |
| 16. | Smoker | ☐ No | | ☐ Social (<5/w) | | ☐ Yes |
| 17. | Your Motivation Level How would you rate your motivation levels generally. | ☐ Low | ☐ Below Average | ☐ Average | ☐ Above Average | ☐ High |

APPARATUS AND METHOD FOR MONITORING STRAIN AND/OR LOAD APPLIED TO A MAMMAL

RELATED APPLICATIONS

The present application is a National Phase entry of International Application Number PCT/AU2005/000743, filed May 25, 2005, which claims priority from, Australian Application Number 2004902785, filed May 25, 2004, the disclosures of which are hereby incorporated by reference herein in their entirety.

BACKGROUND OF THE INVENTION

The present invention relates to apparatus and a method for monitoring strain and/or load applied to the body of a vertebral mammal. The present invention is particularly suitable for monitoring strain and/or load applied to the back of the mammal including the lumbar spine and it will be described herein in this context. Nevertheless, it is to be understood that the present invention is not thereby limited to such applications. In this document use of the words strain and/or load in relation to the body of a mammal includes a reference to movements, muscle forces and loads including gravitational loads acting on the body of the mammal.

Preventing back injuries presents a major workplace safety challenge. According to the Bureau of Labour Statistics in the United States, more than one million workers suffer back injuries each year. Back injuries account for one in every five workplace injuries or illnesses. Moreover, one-quarter of compensation indemnity claims involve back injuries, costing industry billions of dollars on top of the pain and suffering borne by employees.

A documented cause of compensable workplace injuries is due to manual handling tasks such as lifting, placing, carrying, holding and lowering of materials. Statistics show that four out of five injuries are to the lower back and three out of four of such injuries occurred while an employee was lifting. One difficulty in preventing and/or treating lower back injury is due to a lack of facility to objectively measure movements and stresses placed on the lower back over time and therefore the risks that are associated with use of the lower back when undertaking a task or activity that presents a risk of injury.

The present invention may provide a mechanism for avoiding or at the very least minimizing incidence of back injuries and/or may assist rehabilitation of existing injuries by monitoring movements, associated muscle activities and loads experienced by the lumbar spine.

Because preventing a back injury is far preferable to repairing the injury, the present invention may monitor loads placed on a person's back while that person is undertaking a task or activity and may assess whether that load presents a risk of injury. The monitoring may be performed in real time to provide useful feedback to the person so that the person may modify a task or activity being undertaken in a manner that may reduce the load. This may lead to a reduction of the load and a consequent reduction in risk or occurrence of an injury.

SUMMARY OF THE INVENTION

According to one aspect of the present invention there is provided apparatus for monitoring strain and/or load applied to the body of a vertebral mammal, said apparatus including:
a sensor for measuring acceleration of said body relative to an inertial frame of reference and for providing first data indicative of said acceleration, wherein said measuring sensor includes at least one inertial sensor;
a memory for storing said acceleration data at least temporarily; and
a processor for processing said acceleration data to provide a measure of strain and/or load to said body, wherein said processor is adapted to derive angular position from said acceleration data.

The apparatus may further include structure for measuring muscle activity and for providing second data indicative of the muscle activity.

According to a further aspect of the present invention there is provided a method of monitoring strain and/or load applied to the body of a vertebral mammal, said method including:
measuring acceleration of said body relative to an inertial frame of reference and providing first data indicative of said acceleration, wherein said measuring is performed by at least one inertial sensor;
storing said acceleration data at least temporarily; and
processing said acceleration data to provide a measure of strain and/or load to said body, wherein said processing includes deriving angular position from said acceleration data.

The method may further include measuring muscle activity and providing second data indicative of the muscle activity.

Throughout the description and claims an inertial frame of reference denotes a frame of reference in which Newton's laws of motion apply. When no force is being exerted on an object then the object will move inertially. A frame of reference that moves with such an object is an inertial frame of reference. An inertial sensor denotes a sensor that responds to inertial forces such as forces that relate to acceleration of a system or that give rise to a change in velocity.

At least one or each inertial sensor may include at least one accelerometer. The accelerometer may measure linear acceleration of the body or body part with which it is associated. At least one or each accelerometer may include structure for measuring acceleration simultaneously along one, two or three orthogonal axes. Displacement data may be derived from at least one or each accelerometer by a process of integration as is well known in the art. Alternatively or additionally data may be derived from one or more accelerometers to provide angular displacement or position relative to a reference such as a direction defined by gravity. The apparatus may include structure for deriving angular position from the acceleration data such as by calculating a forward tilt angle and a side tilt angle. The apparatus may include structure such as a gyroscope for deriving rotational position of the body part.

Each accelerometer may detect a change in acceleration of a small mass mounted within a micro chip on a PCB board. As the PCB board, and the accelerometer move from one position to another, the mass experiences an acceleration at the start of the movement as well as a deceleration as the movement ceases. The accelerometer may convert movement of the mass into a voltage signal (typically in mV) that represents data in its most raw form. Span and offset adjustments may convert the voltage signal to a G force value, by way of calibration constants. A first calibration constant (p) is known as a 'multiplier' or 'gain' constant and may be derived by means of simultaneous equations wherein signal values equate to G force values. A second calibration constant (o) is known as an offset constant. Once calculated, the calibration constants (p) and (o) may be programmed into software and may become a permanent fixture of the programming. There may be two calibration constants for each channel and three channels per sensor.

Angular displacement of the accelerometer may be calculated by multiplying the raw signal value by the gain constant (p) and adding the offset constant (o). The resulting value may represent the G force acting on one axis. For a resultant G force in three dimensions, three axes trigonometry may be used, wherein x is the horizontal axis, y is the vertical axis and z is the 'through page' axis. Using 3D Pythagoras and an inverse tangent formula, two angles may be derived to give a position for the accelerometer. One accelerometer in isolation may only give a direction of movement, but when there are two accelerometers, the difference between angles of the two accelerometers may represent a change in position (in degrees) of one accelerometer compared to the other accelerometer. This may allow the apparatus to calculate angular position of the lumbar spine, at any moment in time, within a three dimensional axis.

The following expressions may be used to derive angular changes from accelerometers.

$$ep + o = 1 \text{ g}$$

$$fp + o = -1 \text{ g}$$

where:
e=millivolts for 1 g
f=millivolts for −1 g
p=gain (multiplier)
o=offset
Solving p and o:

$$ep + o - fp - o = 2 \text{ g}$$

$$(e - f)p = 2 \text{ g}$$

$$p = \frac{2 \text{ g}}{e - f}$$

$$ep + o = 1 \text{ g}$$

$$o = 1 \text{ g} - ep$$

or $$fp + o = -1 \text{ g}$$

$$o = -1 \text{ g} - fp$$

Note: values for p and o should be calculated for each axis.

$$x_m v p_x + o_x = x_g$$

$$y_m v p_y + o_y = y_g$$

$$z_m v p_z + o_z = z_g$$

The above 3 equations show for the 3 axes the span and offset adjustment which converts millivolts to g.

The magnitude and tilt (forward/side) for the resultant vectors may be calculated as follows.
Magnitude:

$$r_g = \sqrt{x_g^2 + y_g^2 + z_g^2}$$

The magnitude represents the vector sum in three dimensions of the resultant G force.
Forward Tilt:

$$\theta = \tan^{-1}\left(\frac{z_g}{\sqrt{x_g^2 + y_g^2}}\right)$$

The forward and side tilt angles θ, β give the rotational position of the accelerometer relative to the z and x axes respectively.
Side Tilt:

$$\beta = \tan^{-1}\left(\frac{x_g}{\sqrt{z_g^2 + y_g^2}}\right)$$

The structure for measuring position may measure displacement in a lateral or side to side flexion plane. The structure for measuring position may also measure displacement in an extension or front to back flexion plane. The structure for measuring position may include means for measuring rotation. A measure of rotation may be derived from one or more accelerometers, muscle activity and/or one or more gyroscopes.

The structure for measuring muscle activity may include means for measuring surface electromyography (EMG) to establish electrical activity within a muscle. A measure of EMG may be correlated with muscle activity and/or muscle force. The structure for measuring muscle activity may be used to calculate muscle fatigue. The apparatus may include a muscle fatigue algorithm for calculating fatigue level.

The structure for measuring muscle activity may be adapted to measure activity of muscles in the lumbar back, the abdominal region or other muscles that correlate with load on the lumbar spine. In some embodiments activity of muscles may additionally be measured in the biceps of the subject. Measurement of activity in antigravity muscles in an upper limb such as the biceps may assist in resolving ambiguous readings of muscle activity from the back muscles particularly when performing a lifting operation from a fully bent over position. The activity of erector spinae/multifidus and biceps brachii muscles may be measured via recordings of EMG.

The apparatus of the present invention may include means for measuring skin stretch. The means for measuring skin stretch may include a helical coil. When the coil extends, its impedance may change in a reliable and repeatable way. The change in impedance may be measured in any suitable manner and by any suitable means such as means of a bridge circuit.

The memory may receive data from at least one sensor. Each sensor may include or be associated with an analog to digital (A to D) converter. Alternatively, at least one or each sensor may output analog data. The memory device may include or be associated with one or more A to D converters to convert the analog data to a digital domain prior to storing the data. The apparatus may include a digital processor for processing the data. The processor may process the data in real time to provide biofeedback to the person being monitored. The digital processor may include an algorithm for evaluating risk of back injury. The digital processor is programmed with the algorithm perform calculations based on risk assessment principles. The risk assessment may include an evaluation of risk components associated with individual data provided by each measuring means. The risk components may include profile data associated with the person being monitored. Profile data may include personal data and family history which may have a bearing on risk of back strain and/or injury. The cumulative evaluation may be used to provide bio-feedback by various means and may be used as a warning of impending risk and/or retraining system for rehabilitation of an existing injury. The risk components may be combined in accordance with risk assessment principles to provide a cumulative evaluation of risk of back strain and/or injury. The risk components may be combined in a linear or non-linear fashion, eg. weightings may be attributed to the risk components that reflect the contribution that each component makes to the overall assessment of risk. The data storing means may store data in digital format for later analysis and/or reporting. In some embodiments, the memory device includes a memory structure for storing the digital data such as a memory card, a memory stick, or the like. In at least one embodiment, the memory structure is removable to facilitate downloading the data to a remote processing device such as a PC or other digital processing engine.

The system of the present invention may include a user interface means. The user interface means may include a display screen and one or more controls such as buttons or the like to allow the user to interact with the data storing means.

DESCRIPTION OF THE DRAWINGS

A preferred embodiment of the present invention will now be described with reference to the accompanying drawings wherein:

FIGS. 6a to 6d show a circuit diagram associated with accelerometer and gyroscope transducers;

FIGS. 18a to 18c show a sample questionnaire for determining profile data for a person being monitored.

DETAILED DESCRIPTION OF THE INVENTION

Figure 1:
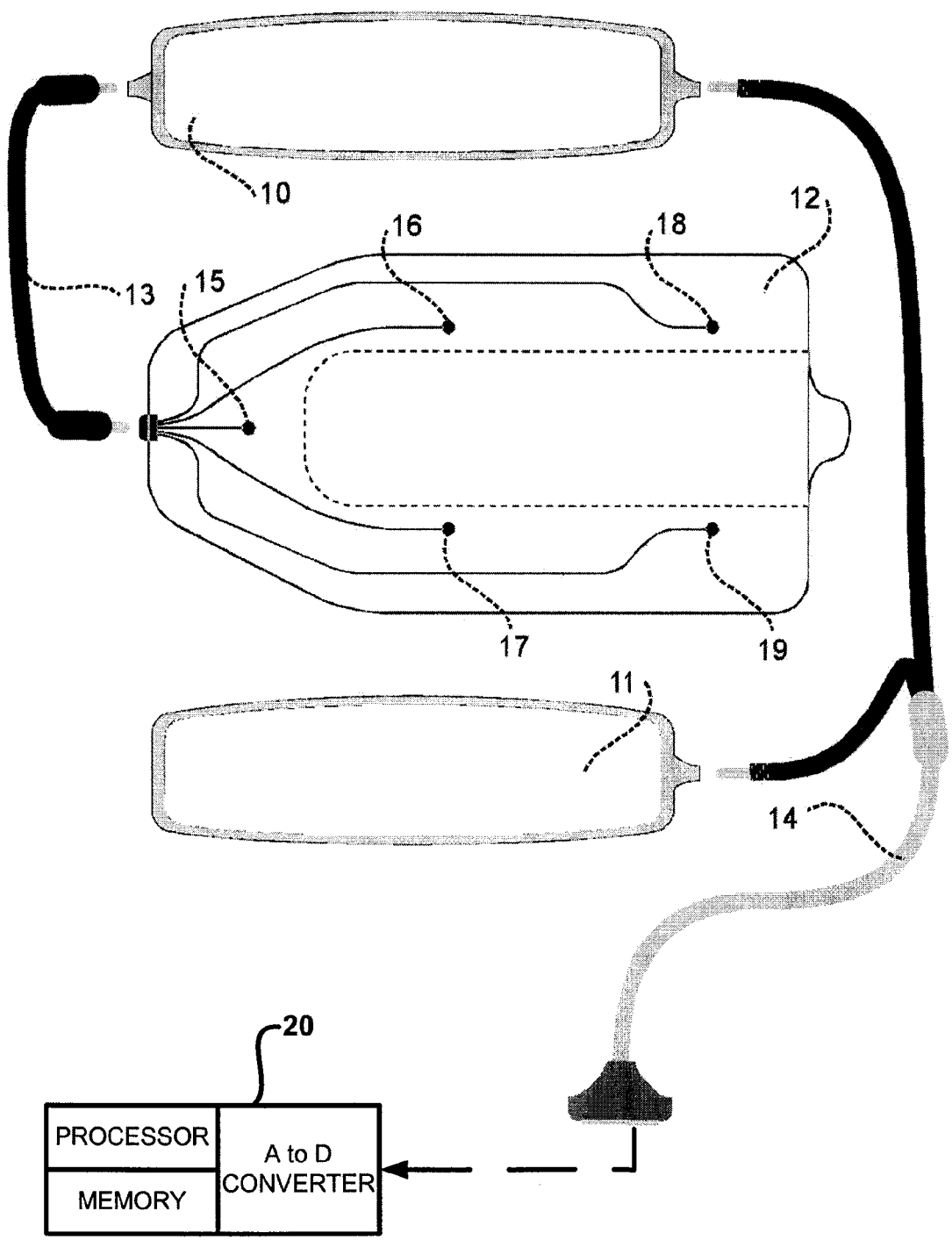
FIG. 1 shows transducer pads and an EMG electrode assembly associated with the apparatus of the present invention.

FIG. 1 shows a pair of transducer pads 10, 11 and an EMG electrode assembly 12. Pads 10, 11 and EMG assembly are connected to a data logger (not shown) via detachable plug in cables 13, 14. Transducer pads are positioned on the back of a person being monitored as described with reference to FIGS. 2A and 2B.

The transducer pads 10, 11 are attached to the skin in any suitable manner such as via adhesive tape. Each transducer pad 10, 11 incorporates one or more accelerometers. Preferably angular changes of lumbar spine orientation are measured by use of four accelerometers, two of which are placed at the upper lumbar spine and other two, at the lower lumbar spine.

If one accelerometer is used in each transducer pad it should be mounted such that it is located centrally over the spine. Each transducer pad 10, 11 may be at least 10 cm wide and may include a gyroscope to provide rotational data.

EMG electrode assembly 12 includes a plurality of EMG electrodes 15-19. Electrodes 16, 17 are adapted to measure muscle activity on the left side of the person's back and electrodes 18, 19 are adapted to measure muscle activity on the right side of the person's back. Electrode 15 is a reference electrode for each circuit associated with EMG electrodes 16-18.

Figure 2A:
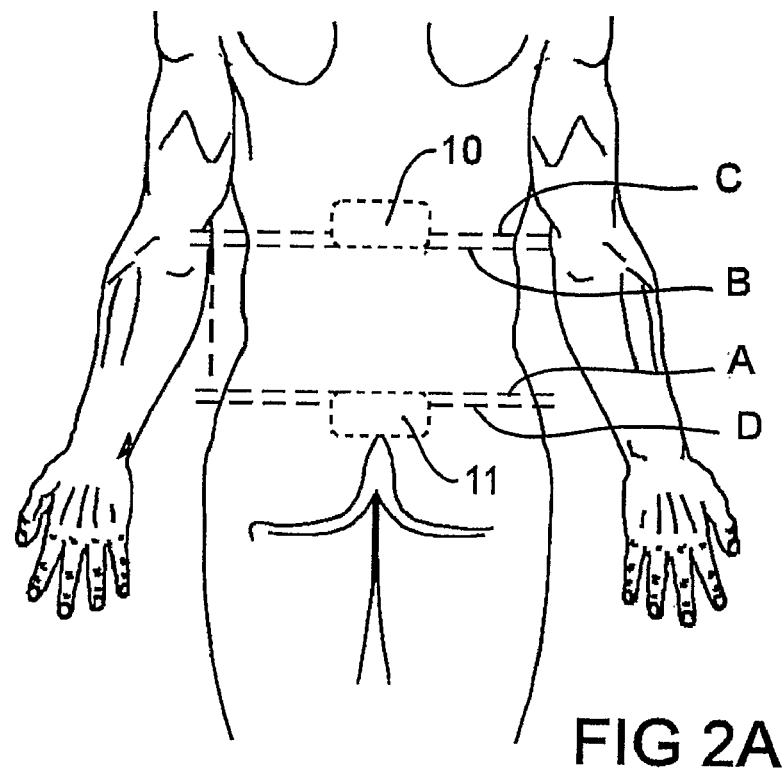
FIGS. 2A and 2B show placement protocols for transducers relative to a persons back.

Referring to FIG. 2A use of the monitoring apparatus requires locating of landmarks on the lower back to ensure reliable readings. The landmarks may be located using the following procedure:

1. The subject should be instructed to stand upright but relaxed;
2. If hair on the lumbar region of the subject has not been clipped, hair clippers may be used to remove excessive hair from the region;
3. An alcohol wipe may be used to clean the skin in the region thoroughly (to remove any oil on the skin);
4. The PSIS (Posterior Superior Iliac Spine) should be located and marked on the left and right sides such that each is the size of an olive;
5. A small horizontal line should be drawn across the middle of each PSIS 'olive';
6. The two horizontal marks should be joined with one extended horizontal line (Line "A") stretching across the spine;
7. After confirming that the subject is in their starting position, a distance of 150 mm up from line "A" should be measured with a soft measuring tape pressed against the subjects skin, gently following skin contours, and marked with a small horizontal line (Line "B");
8. Two less prominent lines 'C' and 'D' should be marked. Line "D" should be 10 mm down from line "A" and Line "C" should be 10 mm up from Line "B".
9. The subject should be instructed to stand with feet shoulder width apart and the distance between the lines "A" and "B" verified;
10. The subject should be instructed to bend forward to their marker, keeping their knees straight.
11. The subject should be instructed to return to their starting position.
12. Adhesive sheets should be placed as follows:
    (a) An adhesive sheet should be prepared by removing the backing;
    (b) The subject should be instructed to bend forward to their marker. When the patient is in this position, the adhesive sheet should be placed such that it's top edge aligns with line "A" (see FIG. 2A). The subject should be instructed to return to their starting position;
    (c) When the subject is upright, the second adhesive sheet should be prepared and placed such that its bottom edge aligns with Line "B".

Figure 2B:
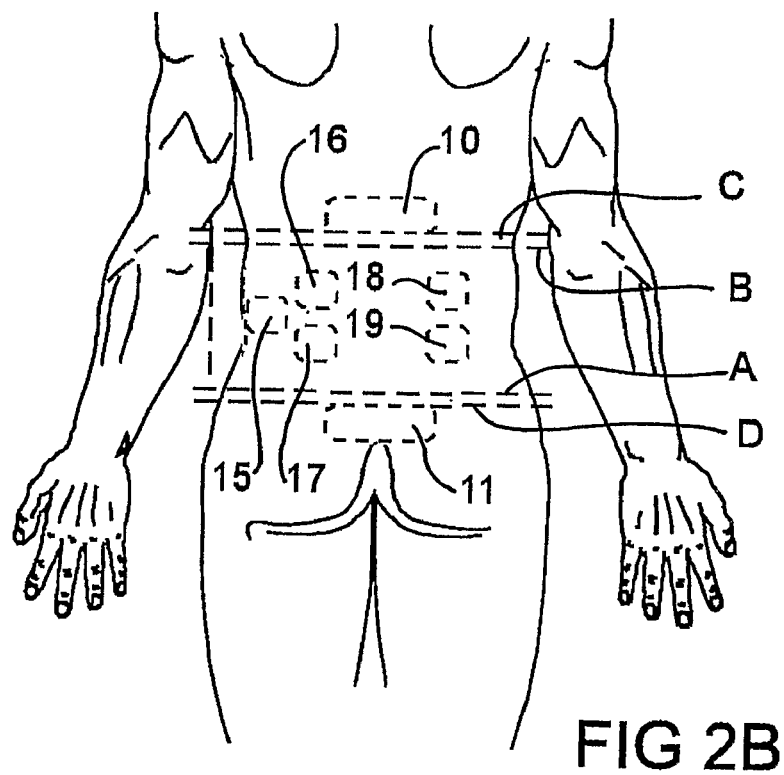

The apparatus of the present invention should be accurately fixed to the back of the person being monitored to minimize reading errors. Referring to FIG. 2B care should be taken in fixing the transducer pads and EMG electrode assembly. Fixation preferably should adhere to the following precautions:

1. Care should be taken not to rotate the accelerometers in relation to each other. If the coil in between them is twisted, it's readings may become unstable.

2. Accelerometer two should be placed lightly on the centre of the spine, with its bottom edge aligned with Line "B". It should be pressed just hard enough to ensure it stays in position.

3. Accelerometer one should be placed lightly on the centre of the spine, with its top edge aligned with Line "A". It should be pressed just hard enough to ensure it stays in position.

4. The subject should be instructed to bend forward to their marker and hold. Whilst the patient is in this position, placement of both accelerometers may be verified. If okay, each accelerometer board should be pressed down firmly to ensure good adhesion. The subject should be instructed to return to their starting position.

5. The subject should be instructed to bend forward to their marker slowly, and return to their starting position. When this is occurring, placement and adhesion of the accelerometer pads should be verified.

Figure 3A:
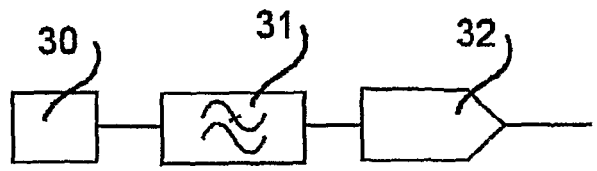
FIG. 3A shows a block diagram associated with an accelerometer transducer.

The diagram shown in FIG. 3A includes accelerometer 30, low pass (averaging) filter 31 and analog to digital (A to D) converter 32. Accelerometer 30 preferably includes a 3D or 3 axes accelerometer such as a Kionix KXM52. Alternatively, accelerometer 30 may comprise a pair of 2D accelerometers such as a device type ADXLZ10E. Each transducer pad 10, 11 may include an accelerometer such as accelerometer 30. Each accelerometer 30 provides outputs that are proportional to acceleration being applied to its respective axes. As gravity provides a constant acceleration of 9.8 m/s2 directly downward, a stable point of reference can be used to determine inclination. By using a minimum of 3 axes, a 3 dimensional vector pointing in the direction of acceleration may be generated. By using two accelerometers, one in each transducer pad, the angle between the accelerometers may be calculated using appropriate software.

Low pass filter 31 provides an averaging function for the accelerometer signal by removing sudden changes in acceleration which may cause aliasing errors. A to D converter 32 provides a digital representation of the accelerometer signal suitable for processing via a digital processor.

Figure 3B:
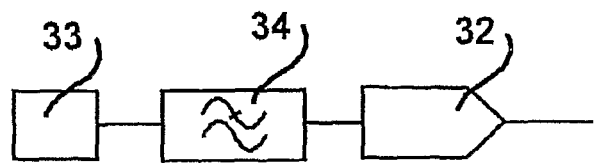
FIG. 3B shows a block diagram associated with a gyroscope transducer.

The diagram shown in FIG. 3B includes gyroscope 33, low pass (averaging) filter 34 and A to D converter 32. Gyroscope 33 preferably includes a device type ADXRS300.

Figure 4:
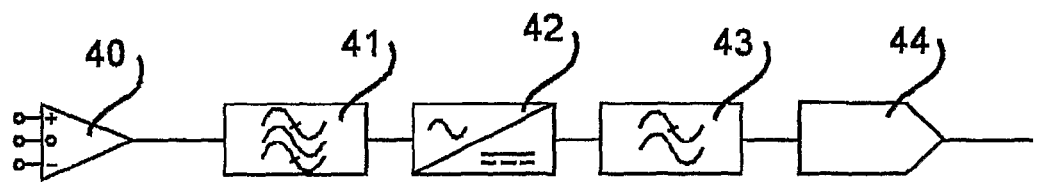
FIG. 4 shows a block diagram associated with an EMG transducer.

The EMG diagram shown in FIG. 4 includes input amplifier 40, filter 41, precision rectifier 42, low pass (averaging) filter 43 and A to D converter 44. Amplifier 40 includes a plurality of inputs for receiving signals from EMG electrodes 15-19. Amplifier 40 includes highly sensitive inputs for amplifying the very small signals produced from electrodes 15-19. Low pass filter 43 removes unwanted portions of the frequency spectrum. Filter 41 may include a band pass filter. A to D converter 44 provides a digital representation of the EMG signal suitable for processing via a digital processor.

Figure 5:
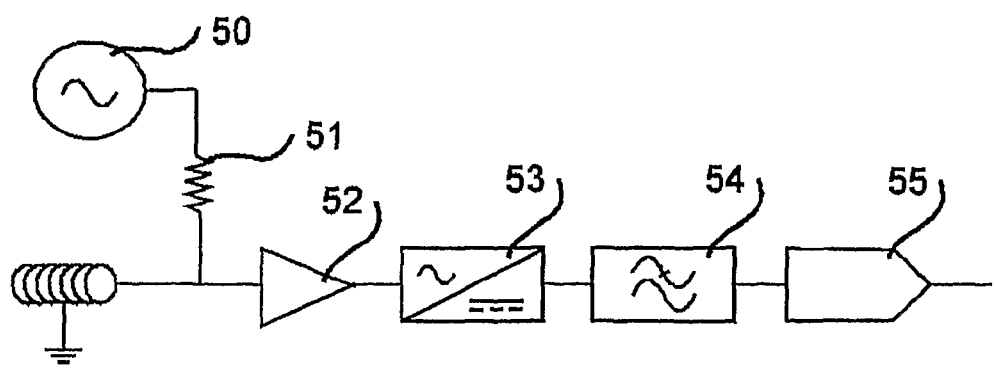
FIG. 5 shows a block diagram associated with a flexion transducer.
Figure 6A:
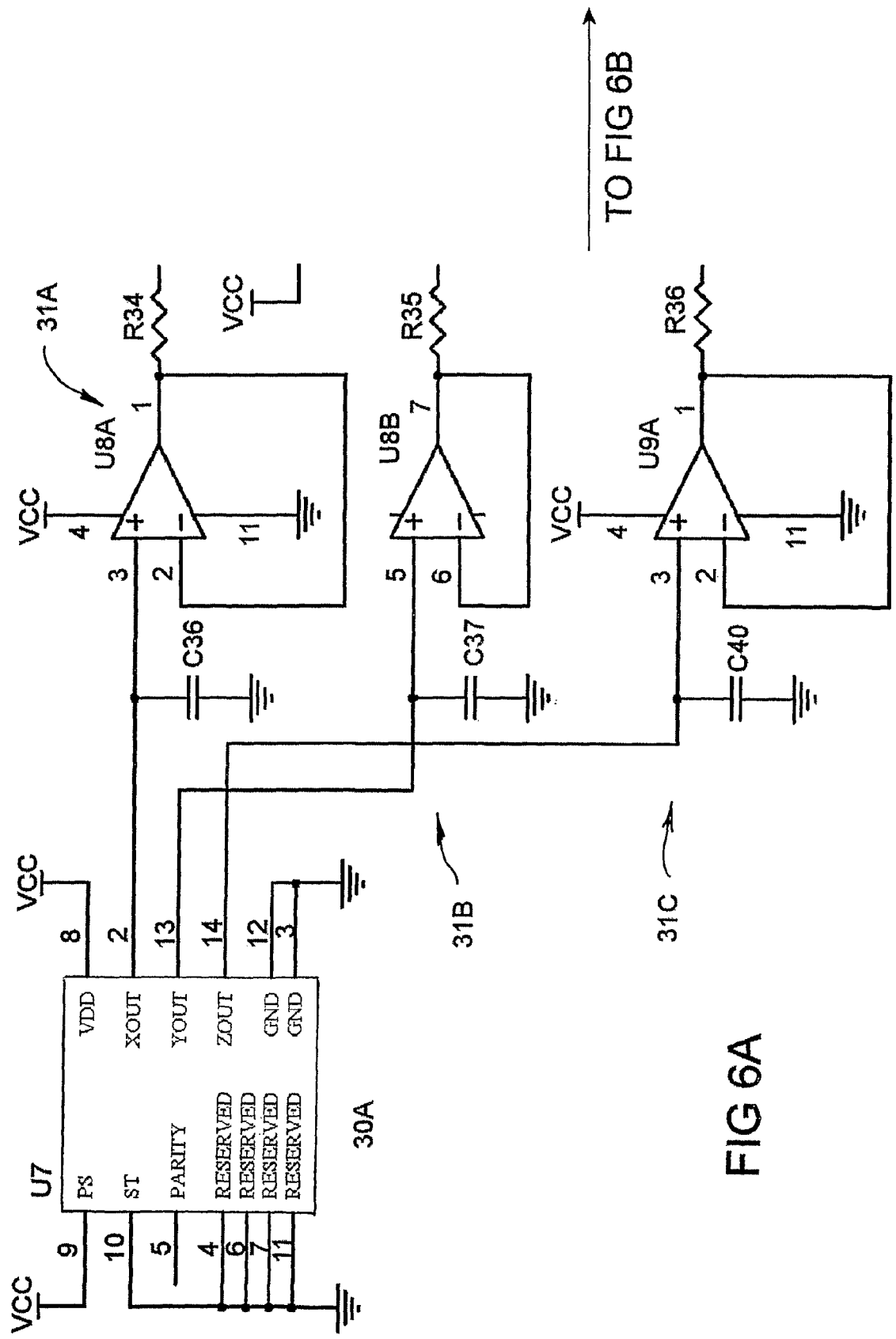
Figure 6B:
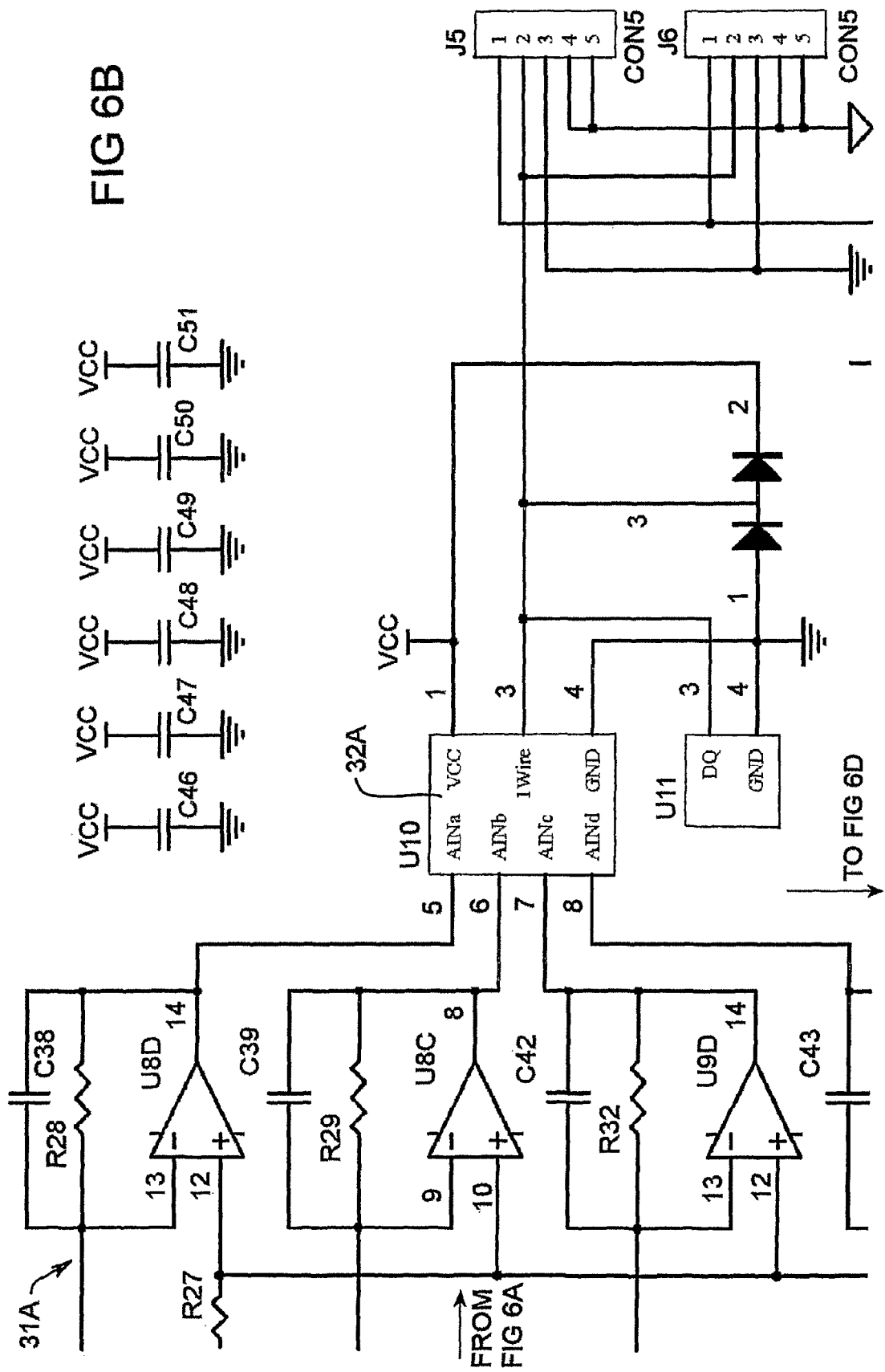
Figure 7A:
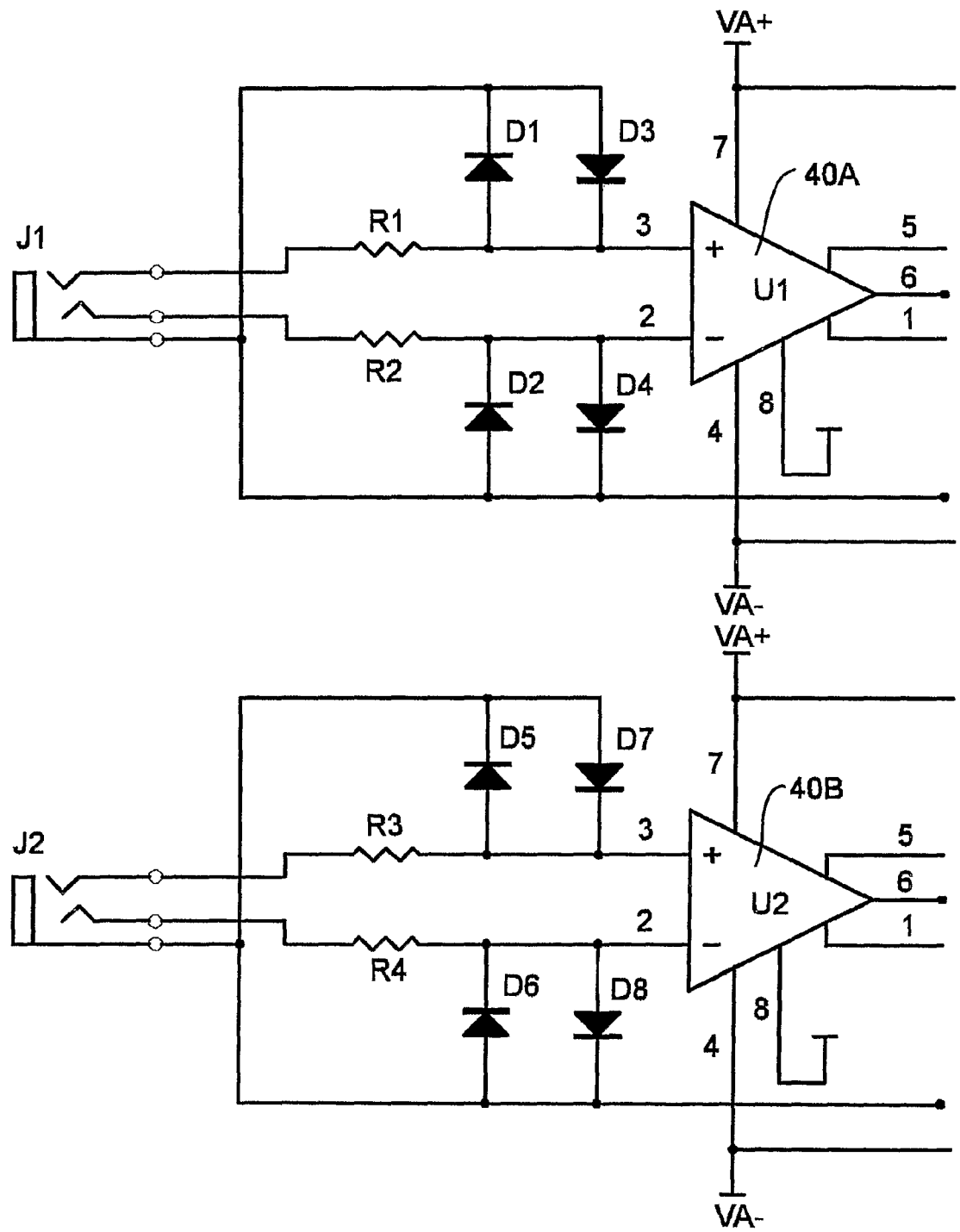
FIGS. 7a to 7d show a circuit diagram associated with an EMG transducer.
Figure 7B:
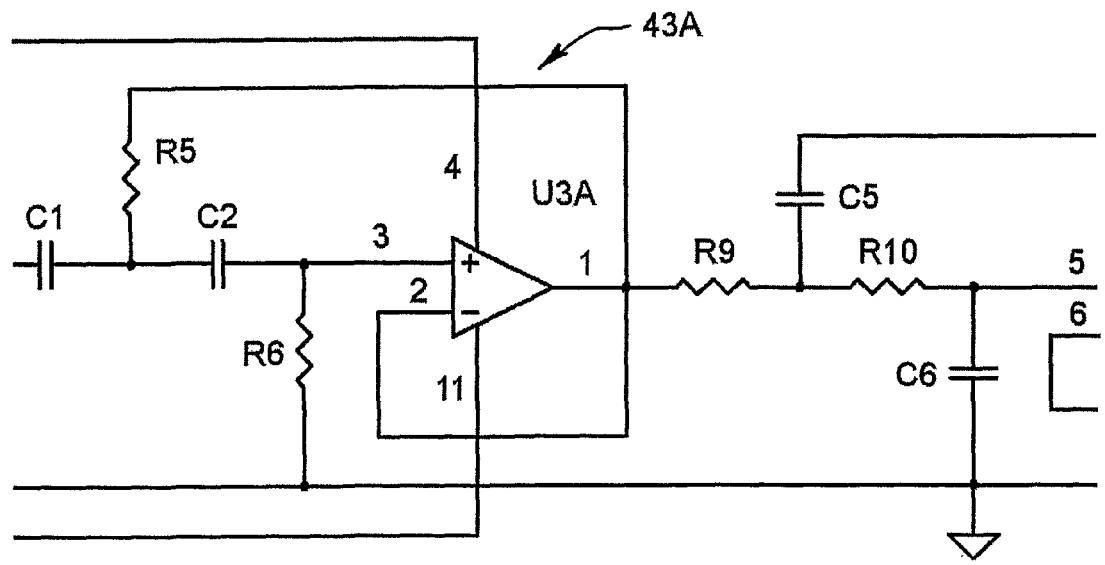
Figure 7B:
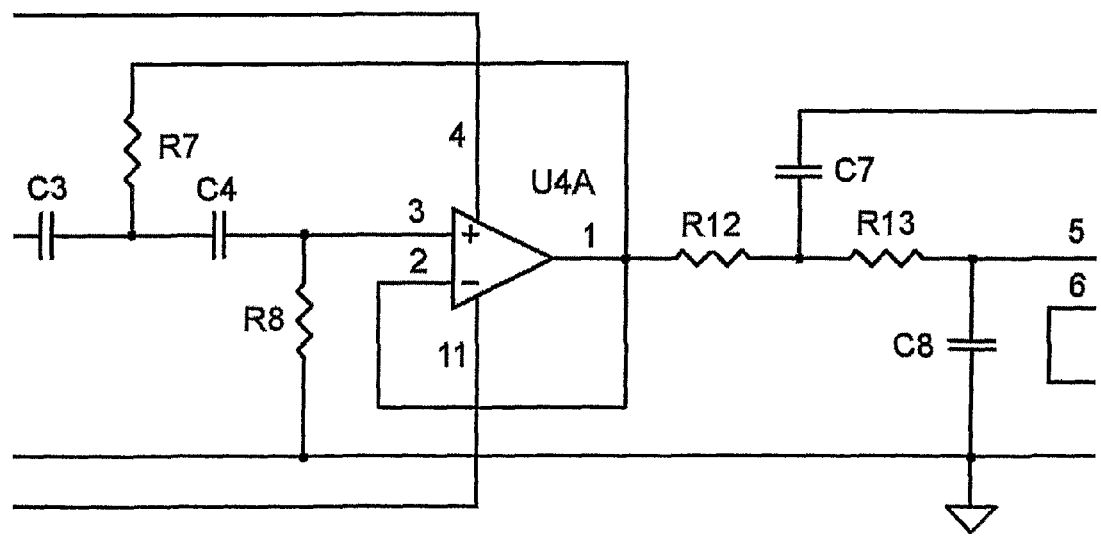
Figure 7C:
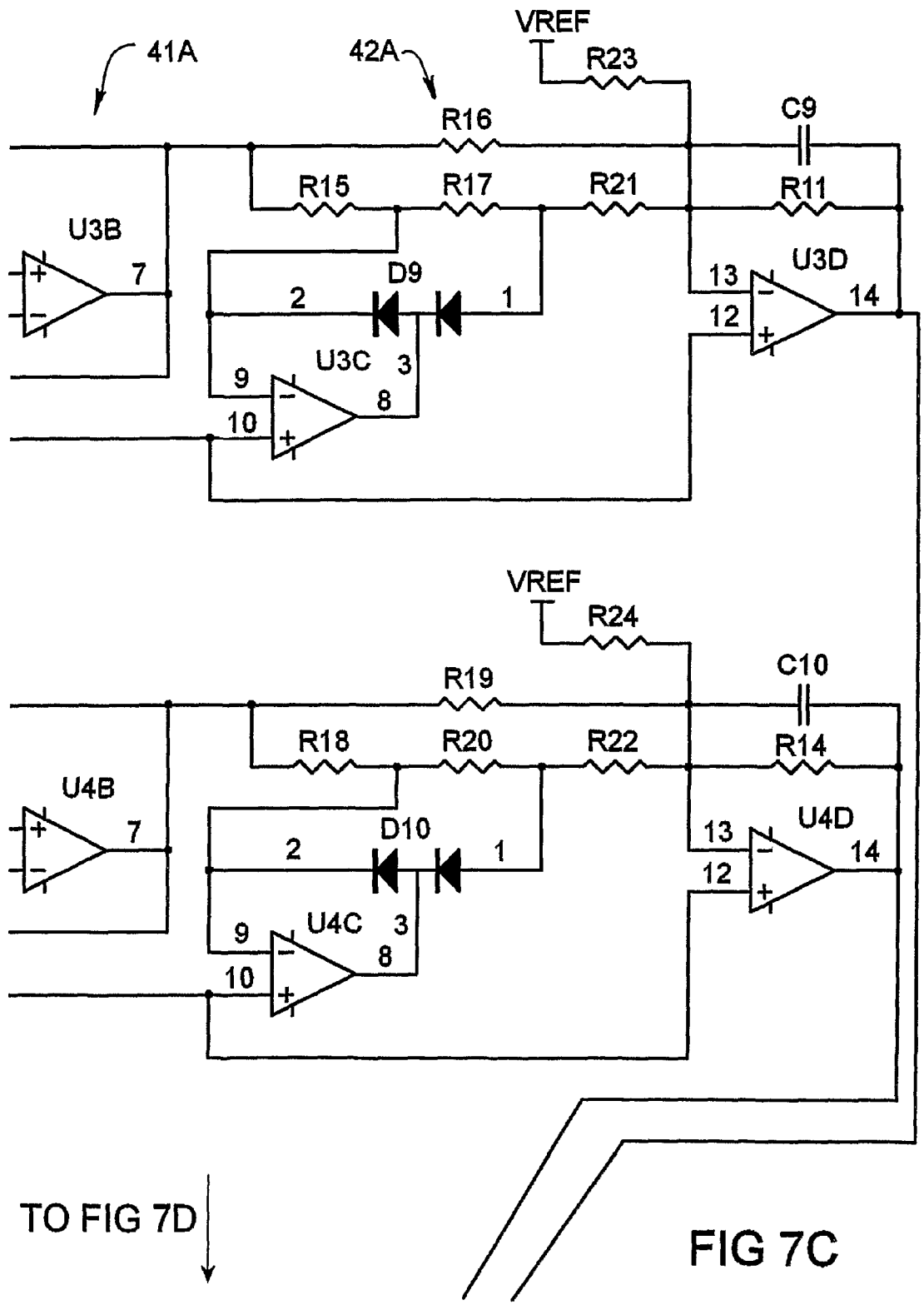
Figure 7D:
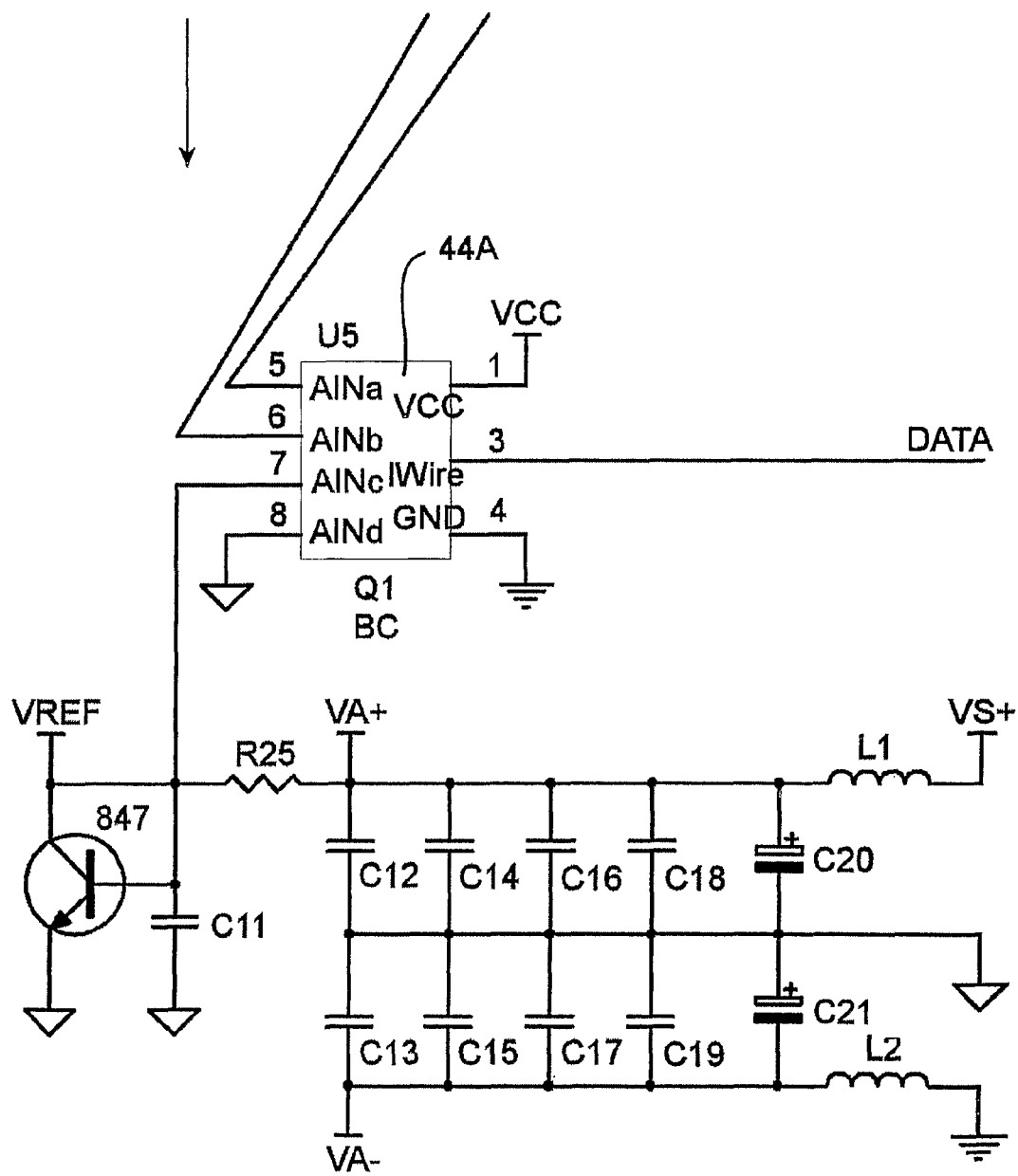
Figure 8A:
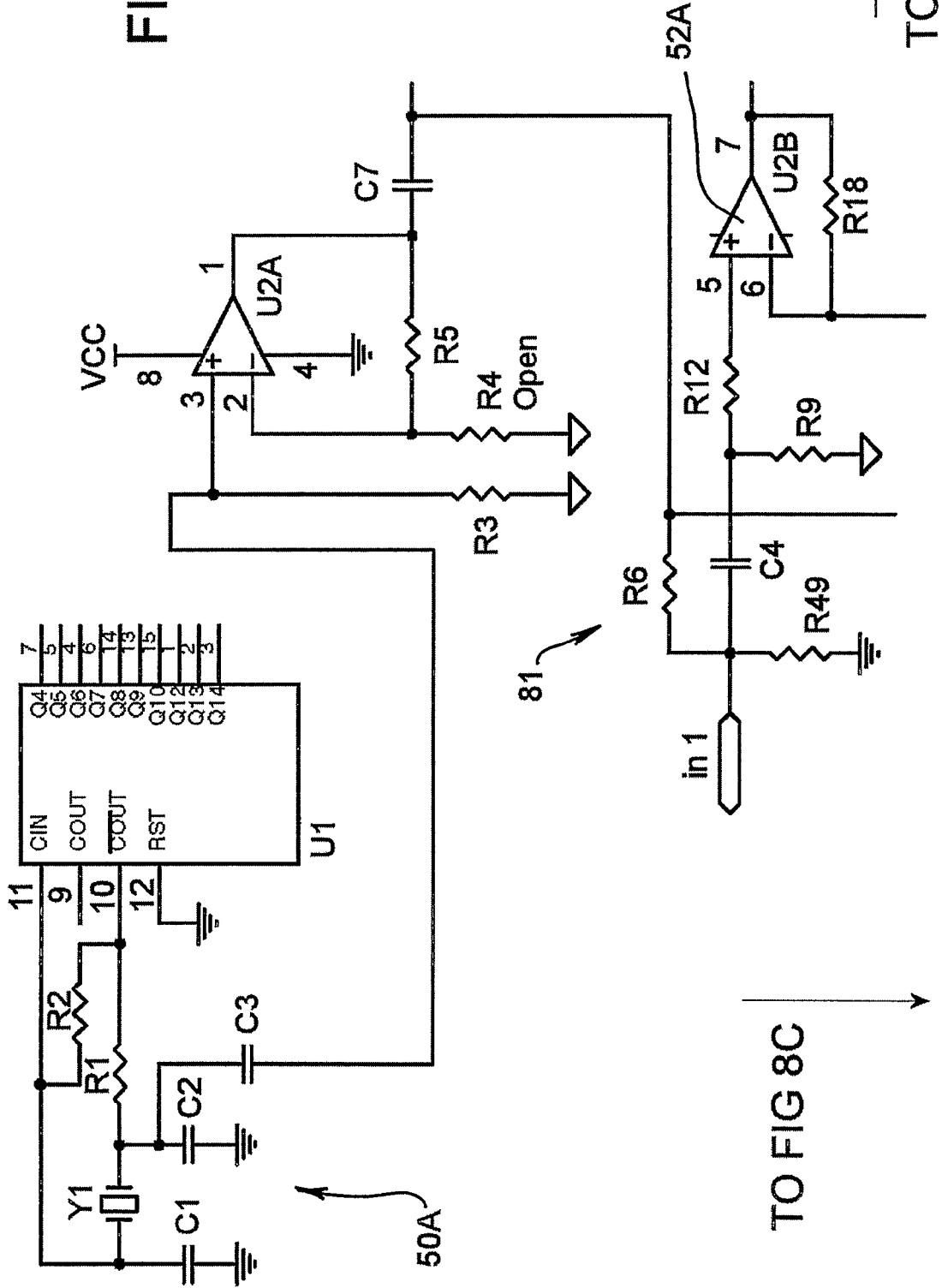
FIGS. 8a to 8d show a circuit diagram associated with a flexion transducer.
Figure 8B:
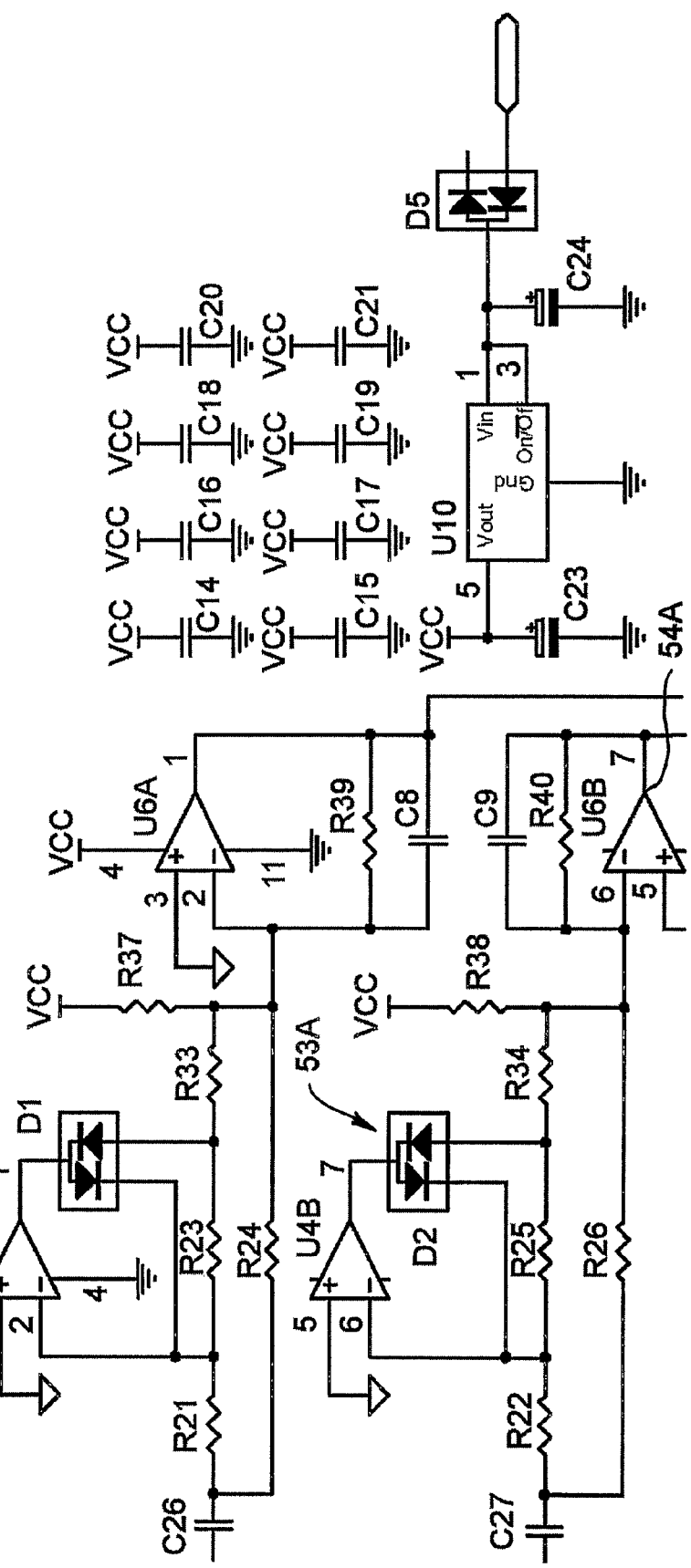
Figure 8C:
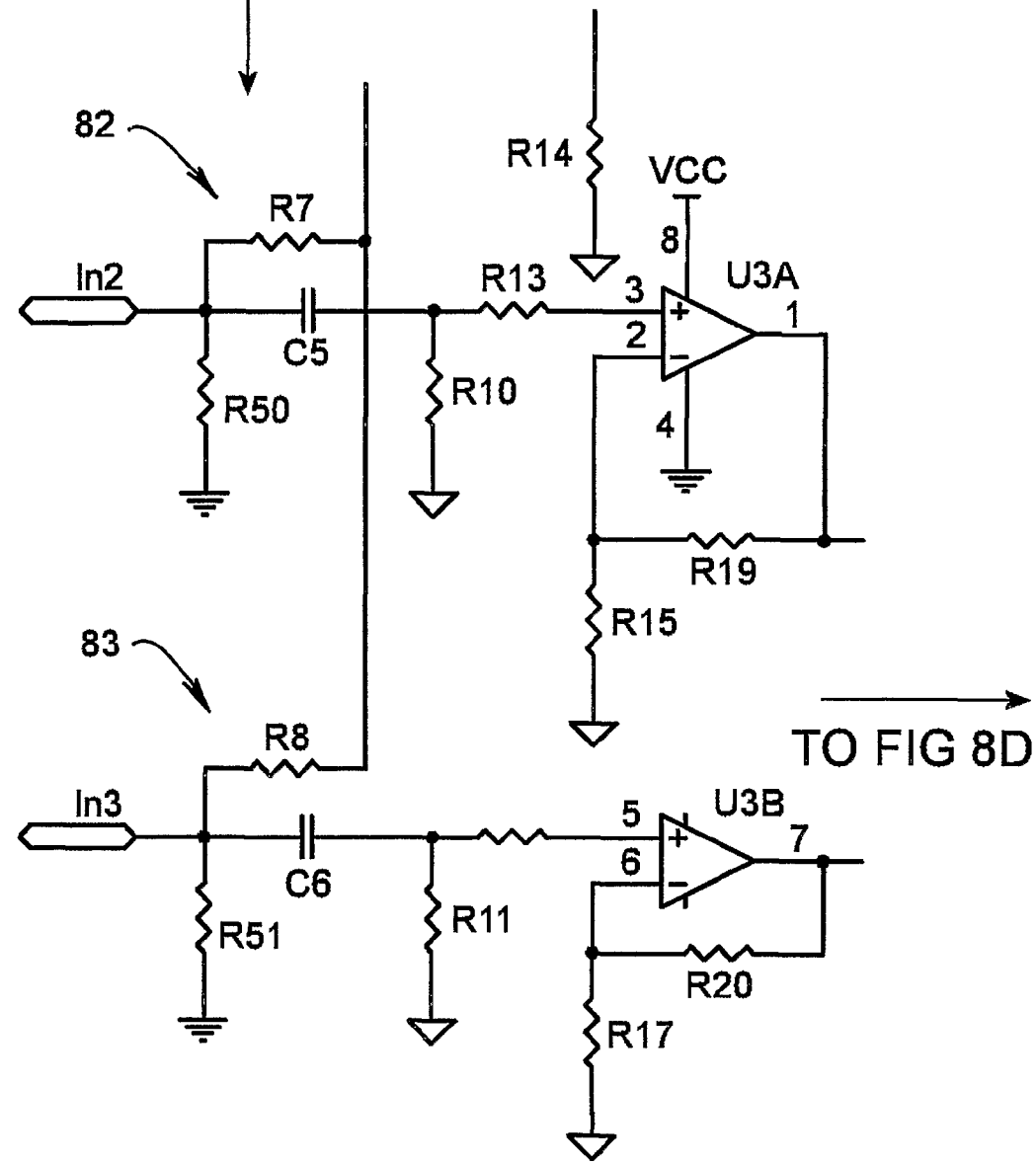
Figure 8D:
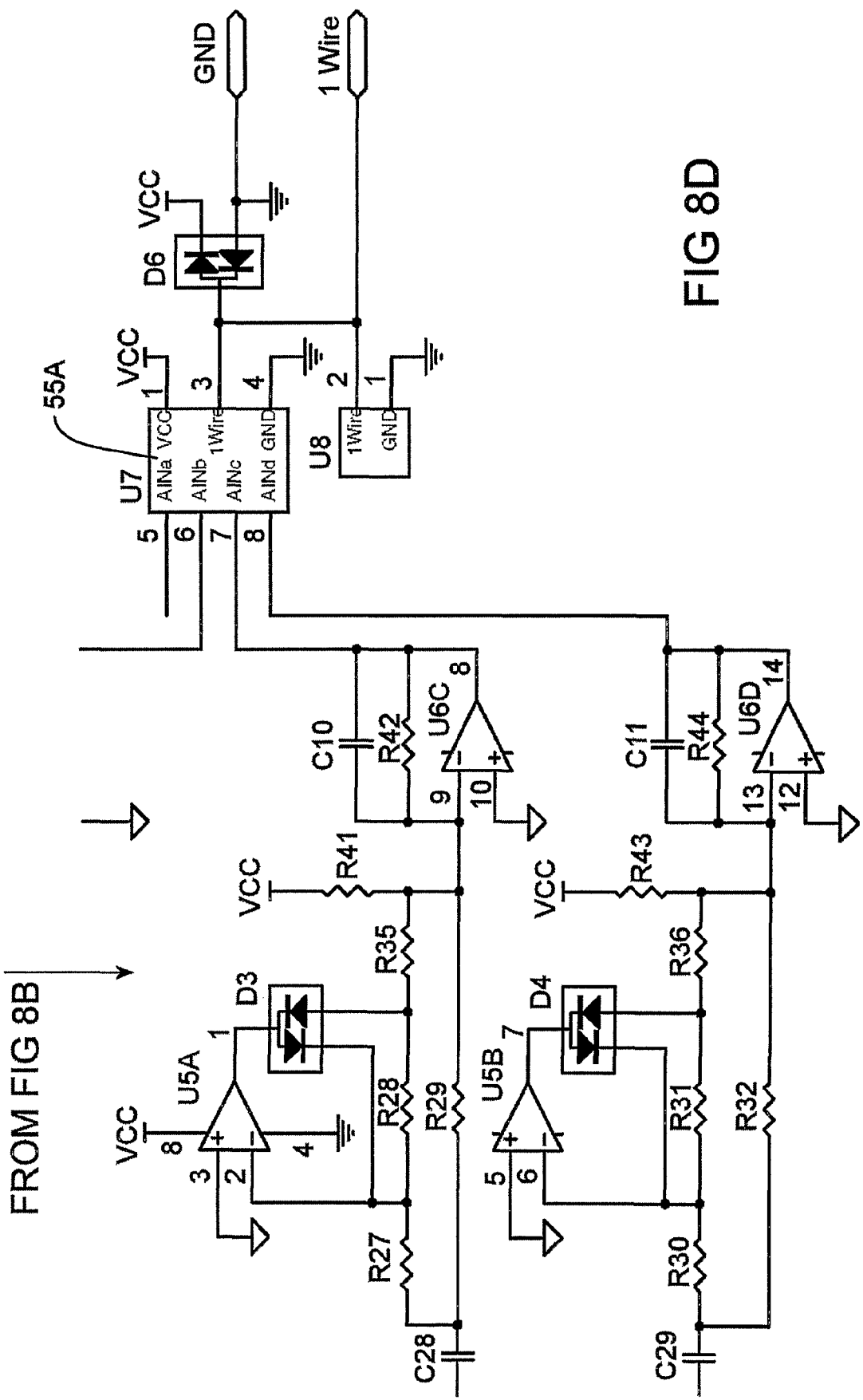

The flexion diagram shown in FIG. 5 includes oscillator 50, resistor 51, amplifier 52, precision rectifier 53, low pass (averaging) filter 54 and A to D converter 55. Oscillator 50 provides an AC excitation voltage for a flexion sensor 56 such as a helical coil of wire. The coil of wire forms an inductor. Many variables affect the value of the inductance such as coil length. By stretching and contracting the coil the inductance is varied. The impedance of the coil is proportional to inductance according to the formula:

$$X_L = 2\pi f L$$

wherein $X_L$=impedance, f=oscillator frequency, and L=the coil inductance.

Oscillator 50 should be stable in amplitude and frequency. Resistor 51 may be arranged to form with the flexion sensor 56, a voltage divider. As the value of resistor 51 is constant, the input voltage to amplifier 52 is controlled entirely by the changing impedance of the flexion sensor 56. Low pass filter 54 is an averaging filter and is used to remove sudden changes in the impedance of the flexion sensor 56. A to D converter 55 provides a digital representation of the flexion impedance signal suitable for processing via a digital processor.

The diagram shown in FIGS. 6a to 6d includes accelerometer package 30A. Accelerometer package 30A may be a device type KXM52-L20 or equivalent. The output of each channel (x, y, z axes) of accelerometer 30A is connected to a respective low pass filter 31A, 31B, 31C. The output of each filter 31A, 31B, 31C is connected to a respective input of A to D converter 32A. A to D converter 32A may be a device type DS2450S. The diagram also includes a gyroscope circuit 33A including an angular rate sensor such as a device type ADXRS300. The gyroscope circuit 33A provides orientation reference data for calculating changes in body position. The output of gyroscope circuit 33A is connected via low pass filter 34A to an input of A to D converter 32A. The output of A to D converter 32A is in a digital format and is connected to a digital processing circuit (not shown) such as a microprocessor. The digital output may be connected to a PC via a suitable interface.

The EMG circuit shown in FIGS. 7a to 7d includes input amplifiers 40A and 40B. Each input amplifier 40A, 40B receives an input from a respective pair of electrodes 15-16 and 15-17 associated with EMG electrode assembly 12. The output of input amplifier 40A passes via low pass and high pass filters 43A, 41A to rectifier and integrator 42A. The output of rectifier and integrator 42A is applied to one input of A to D converter 44A. The output of input amplifier 40B passes via a similar low pass and high pass filter and rectifier and integrator and is applied to a respective input of A to D converter 44A. The output of A to D converter 44A is in a digital format and is connected to a digital processing circuit as described above. A second EMG circuit similar to that shown in FIGS. 7a-7d is used to interface pairs of electrodes 15-18 and 15-19 associated with EMG electrode assembly 12 to the digital processing circuit.

The flexion circuit shown in FIGS. 8a to 8d includes crystal controlled oscillator 50A. The output of oscillator 50A is applied to respective inputs (In1-In3) of flexion channels 81, 82, 83. Flexion channel 81 includes a resistive divider comprising resistors R6, R49. One arm of the divider is connected to a channel of a flexion coil (not shown). An output of the divider is connected to amplifier 52A. The output of amplifier 52A is connected via rectifier circuit 53A to low pass filter 54A. The output of filter 54A is connected to one input of A to D converter 55A. Flexion channels 82, 83 are configured similarly to flexion channel 81 and will not be described in detail. The outputs of flexion channels 82, 83 are connected to respective inputs of A to D converter 55A. The output of A to D converter 55A is in a digital format and is connected to a digital processing circuit as described above.

Digital data from the accelerometer, EMG and flexion circuits is processed in the digital domain via a digital processing engine such as a suitably programmed microprocessor or the like. The microprocessor may be included with the data logger or it may be located remotely from the data logger. Data may be processed in real time to provide real time feedback to the person being monitored. The feedback may include a measure or evaluation of risk of back strain and/or injury based on the data collected during a predetermined time frame(s). Alternatively, the data may be processed offline to provide an assessment of activities logged during a preceding time frame(s) such as a day's activities with respect of risk of back strain and/or injury.

The digital processing engine may be programmed with suitable software for evaluating risk of back strain and/or injury. The software may determine risk components associated with data provided by the accelerometer, EMG, flexion and other circuits as appropriate. The risk components may be combined in accordance with risk assessment principles to provide a cumulative measure of risk of back strain and/or injury. The risk components may be combined in a specific algorithm to give a risk score that is accumulated per unit of time, such as per second, for an entire time that a monitoring device is worn by a person. The accumulated or aggregate score may be matched to the wearer's personalized preset thresholds. When the aggregate or accumulated score reaches personalized risk thresholds, biofeedback (vibrational, visual and/or auditory) may be triggered. There may be more than one theme of biofeedback. For example, feedback may be based on an hourly aggregate score and on a further aggregate score calculated over a shorter time frame such as a sliding five minute window. The different themes have regard to the fact that risk of injury may arise from a variety of contributing events including events associated with a short burst or bursts of relatively intensive activity as well as events associated with longer periods of less intensive activity that present significant risk when accumulated over a period such as an hour or more.

Flow charts illustrating examples of software for processing data from the accelerometer, EMG and flexion circuits are shown in FIGS. 9 to 17. The software may be adapted for calculating a cumulative score indicative of risk of back strain and/or injury.

Figure 9A:
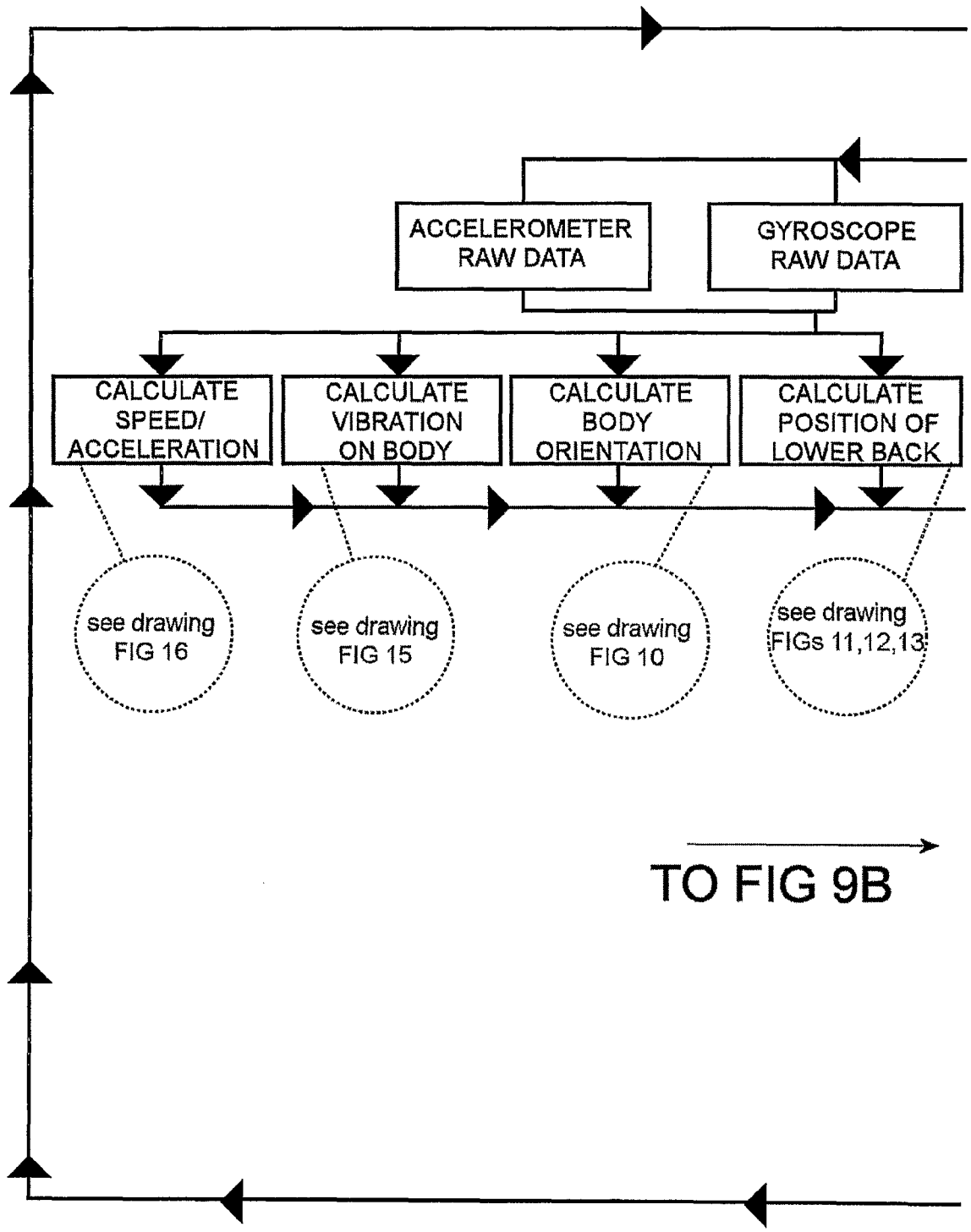
FIGS. 9a to 9c show a flow diagram of processing software associated with the apparatus of the present invention.
Figure 9B:
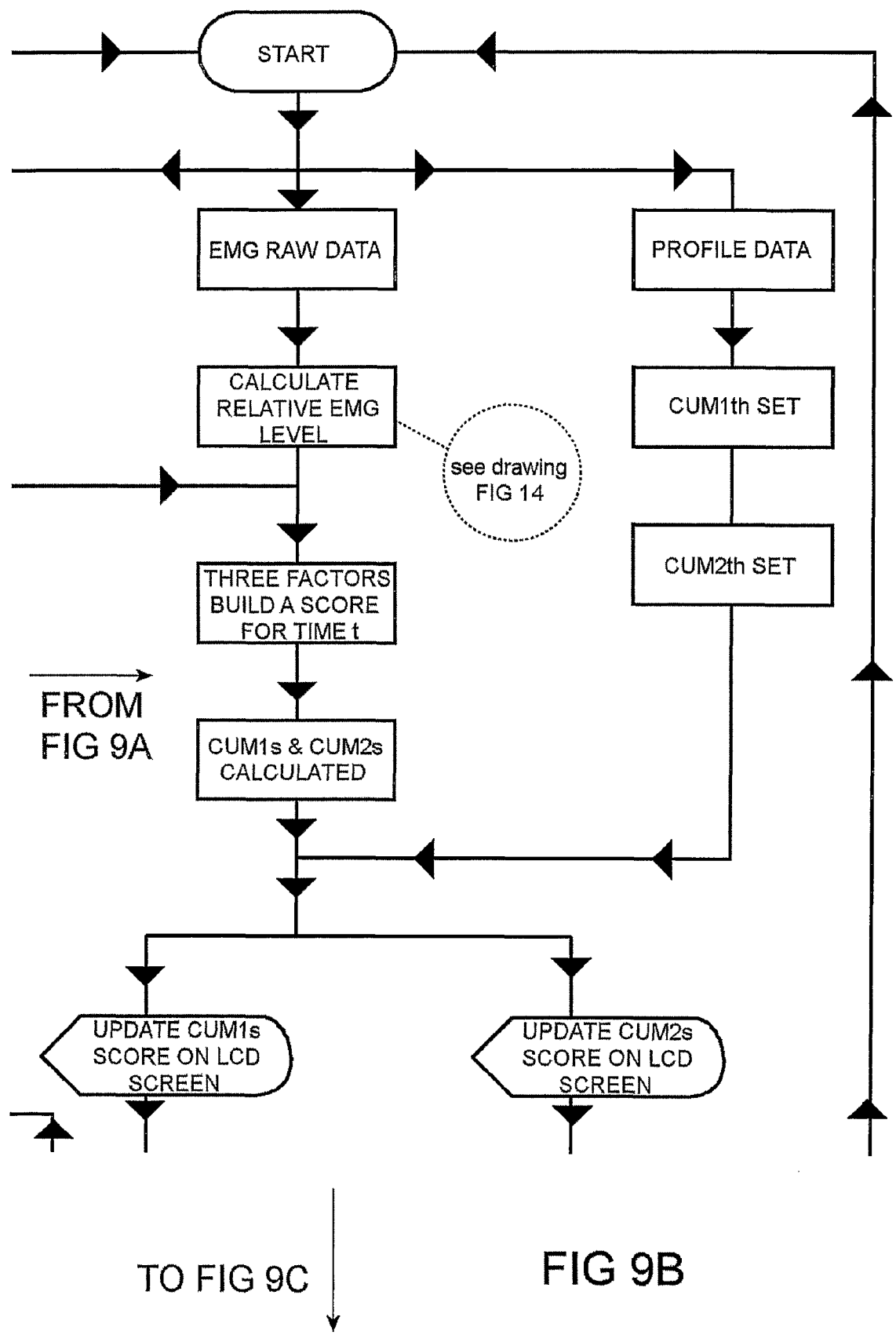
Figure 9C:
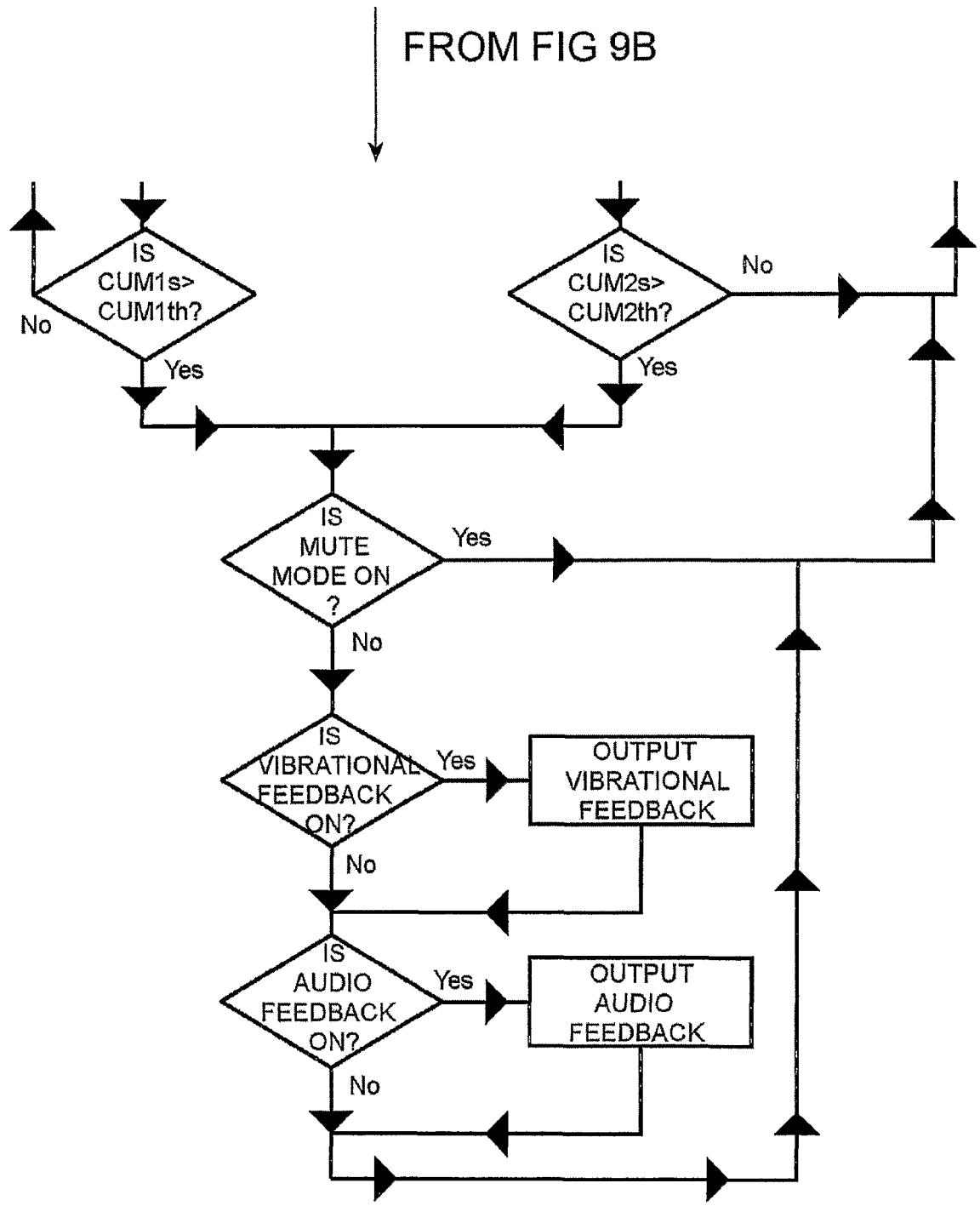
Figure 10A:
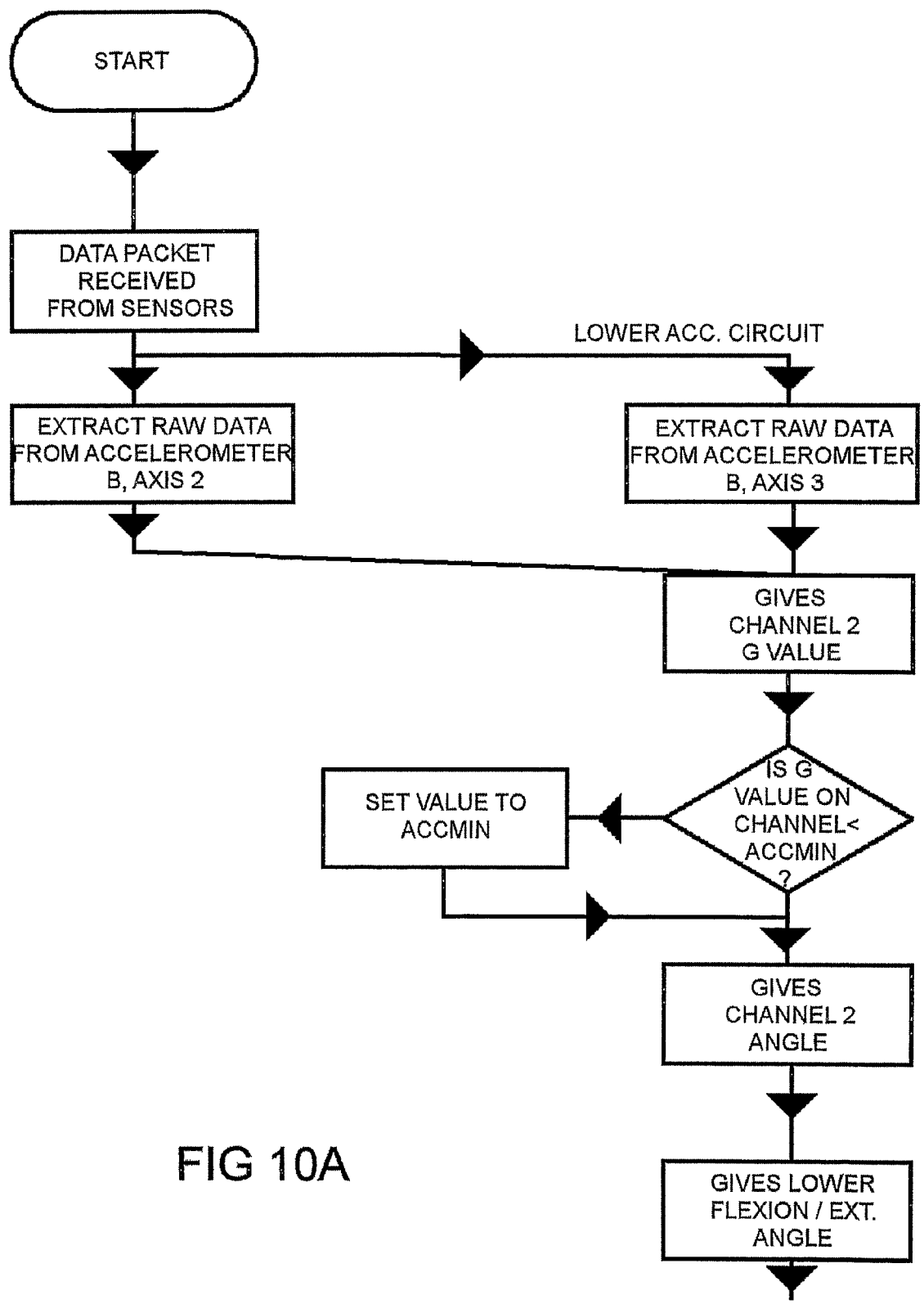
FIGS. 10a and 10b show a flow diagram of software for calculating body orientation.
Figure 10B:
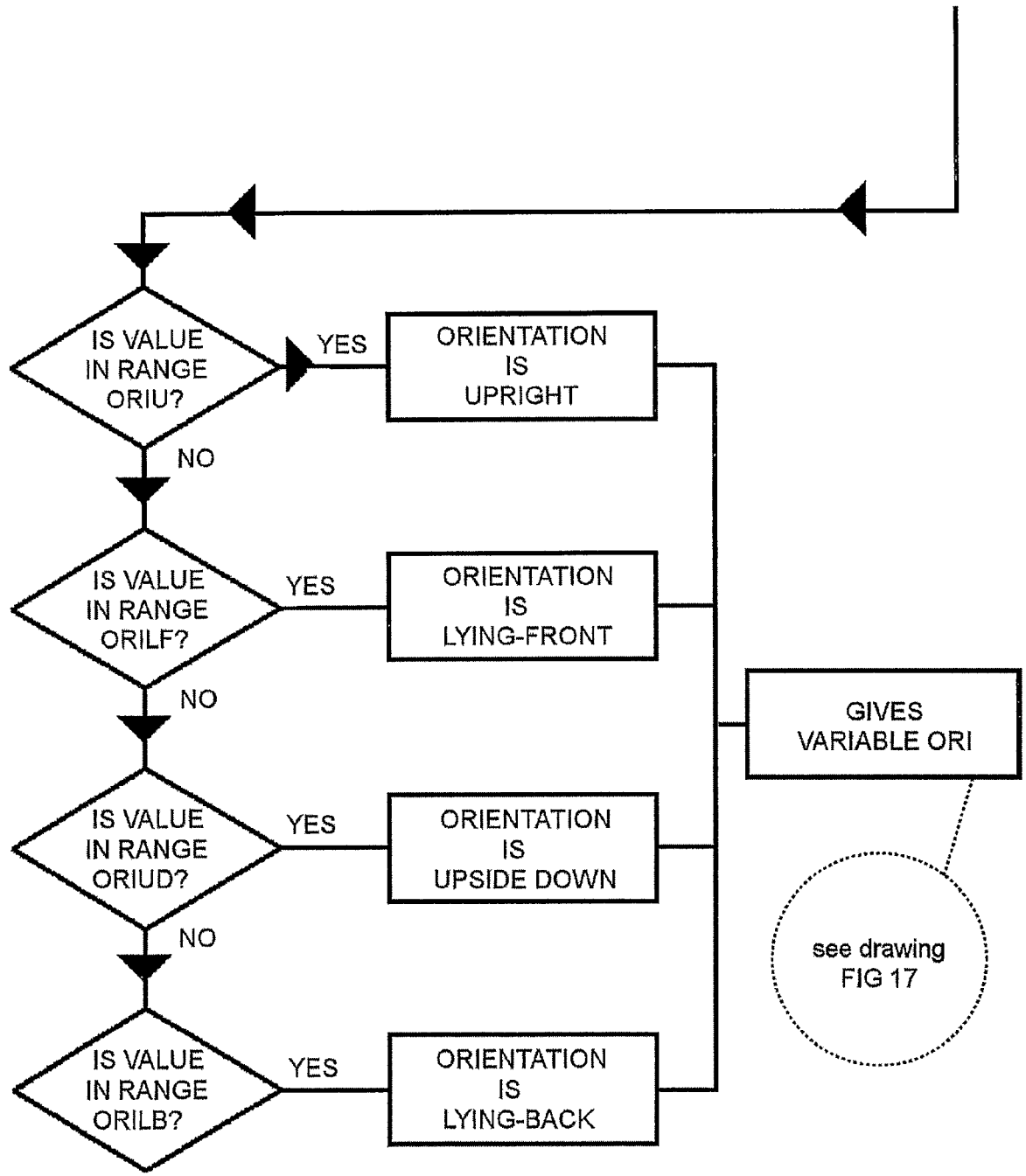
Figure 11A:
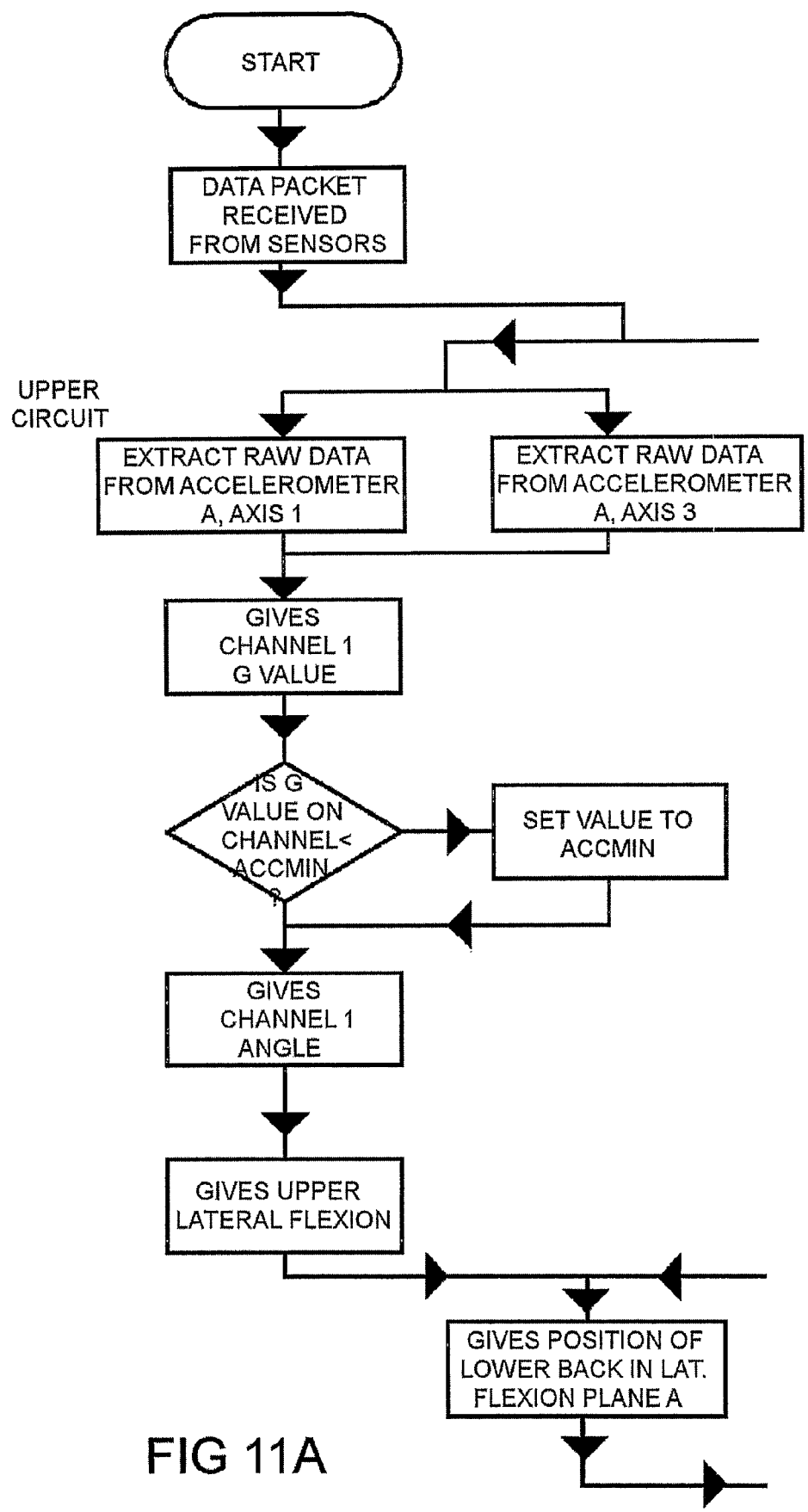
FIGS. 11a and 11b show a flow diagram of software for calculating position of a lower back in a lateral flexion plane.
Figure 11B:
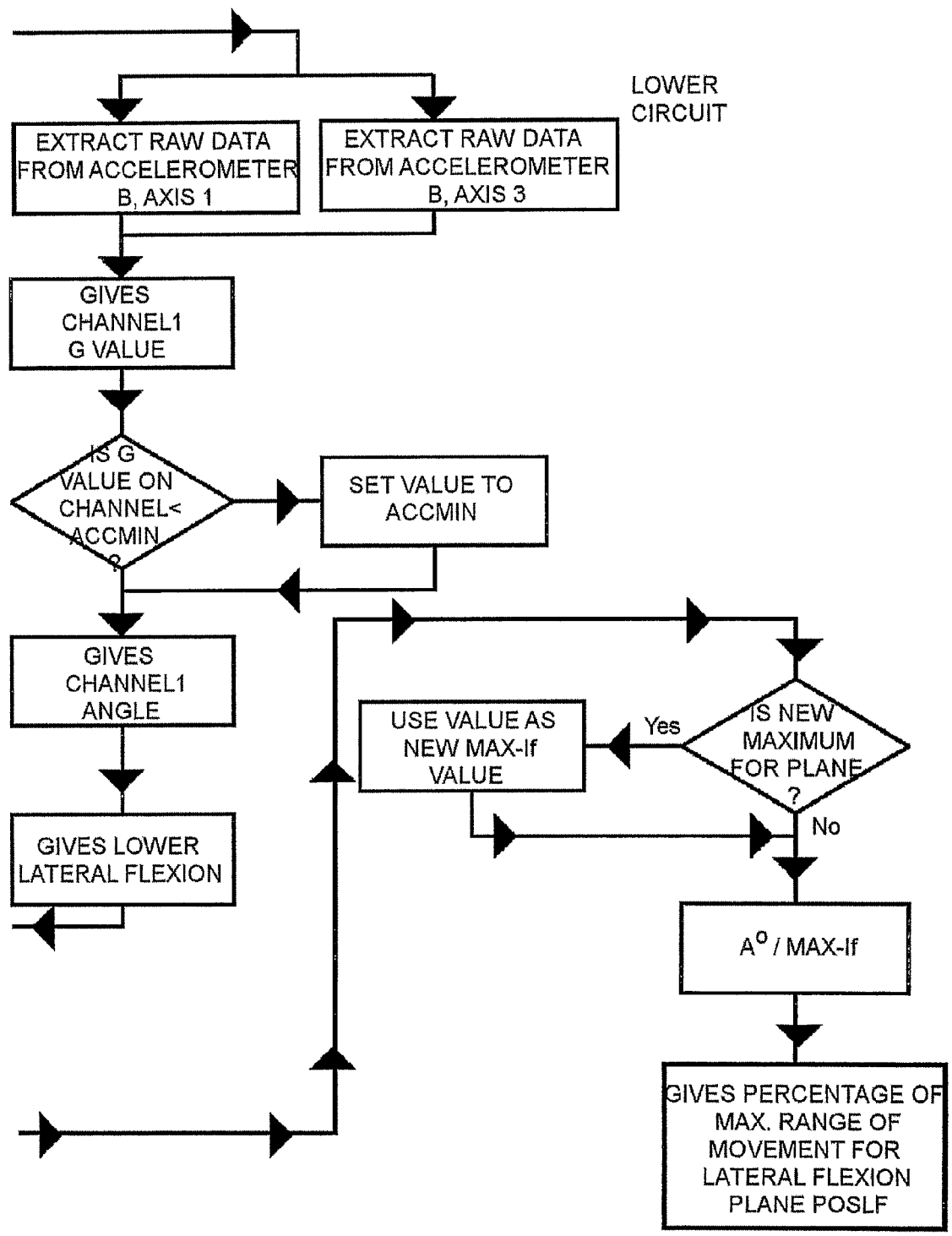

In FIG. 9
  t=period of time to which a data sample relates
  S=Sample Rate
  CUM1$t$=Period of time in seconds of the 1$^{st}$ cumulative feedback window.
  CUM1#=Number of data samples in the 1$^{st}$ cumulative feedback
  CUM1#=6,000
  CUM1$s$=Result of Data Scores for the period CUM1$t$
  CUM1$th$=Threshold Score for the period CUM1$t$
  CUM2$t$=Period of time in seconds of the 2$^{nd}$ cumulative feedback window.
  Number of data samples in the 1$^{st}$ cumulative feedback window. eg. for 60 minutes window at sample rate of 20 Hz.
  CUM2#=72,000
  CUM2$s$=Result of Data scores for the period CUM2$t$
  CUM2$th$=Threshold Score for the period CUM2$t$ In FIG. 10
  ACCMIN=Minimum usable value for accelerometer output
  ORIU=Range of degrees in which body is upright
  ORILF=Range of degrees in which body is lying on front
  ORILB=Range of degrees in which body is lying on back
  ORIUD=Range of degrees in which body is upside down In FIG. 11
  $POS_{LF}=A°$
  MAX-lf
  Where:
  POSLF=Position in the Lateral Flexion Plane
  A°=Relative Angle of the Lower Back in the Lateral Flexion Plane
  MAX-lf=Maximum Range of Movement to date in the Lateral Flexion Plane
  ACCMIN=Minimum usable value for accelerometer output.

Figure 12A:
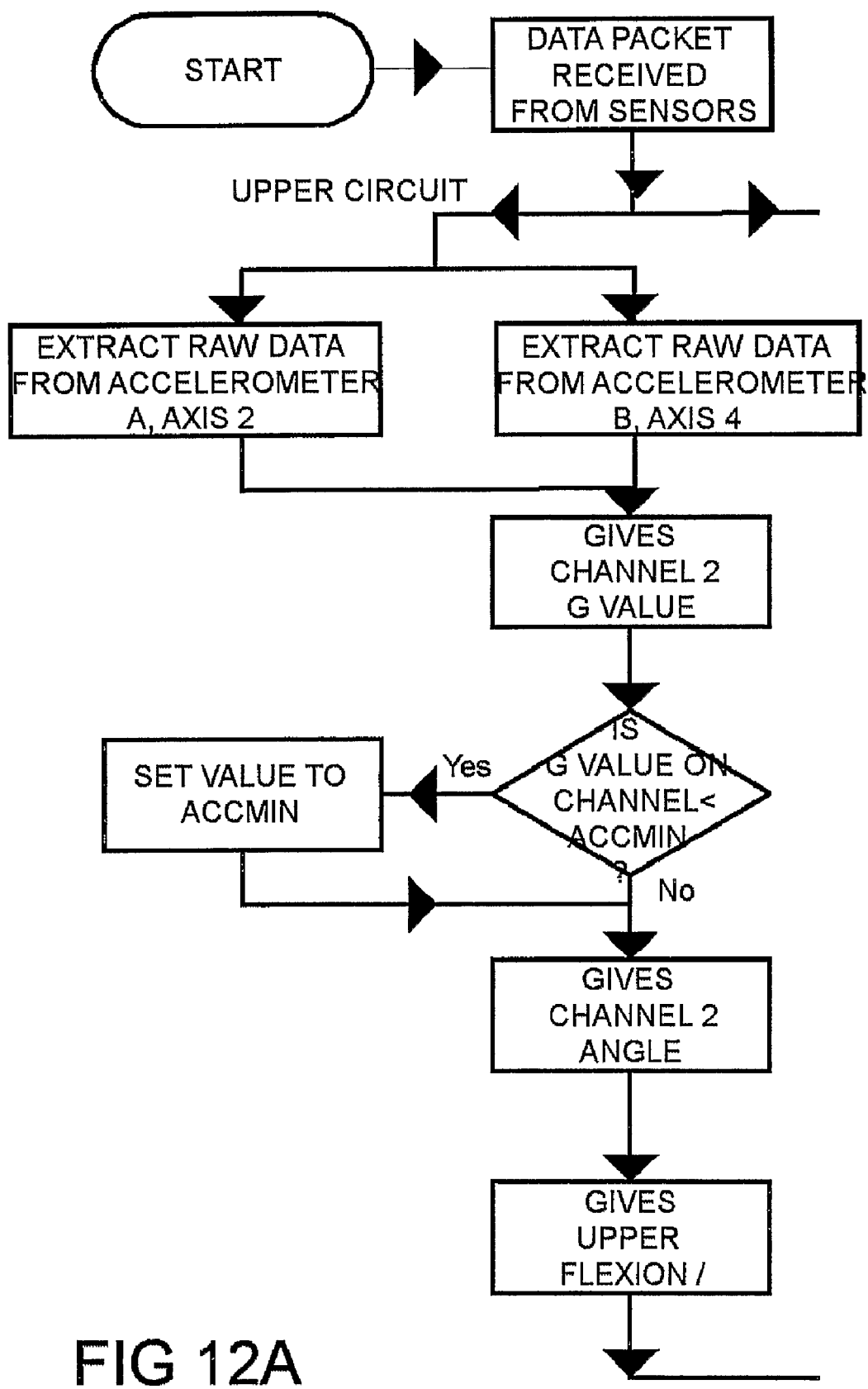
FIGS. 12a and 12b show a flow diagram of software for calculating position of a lower back in an extension flexion plane.
Figure 12B:
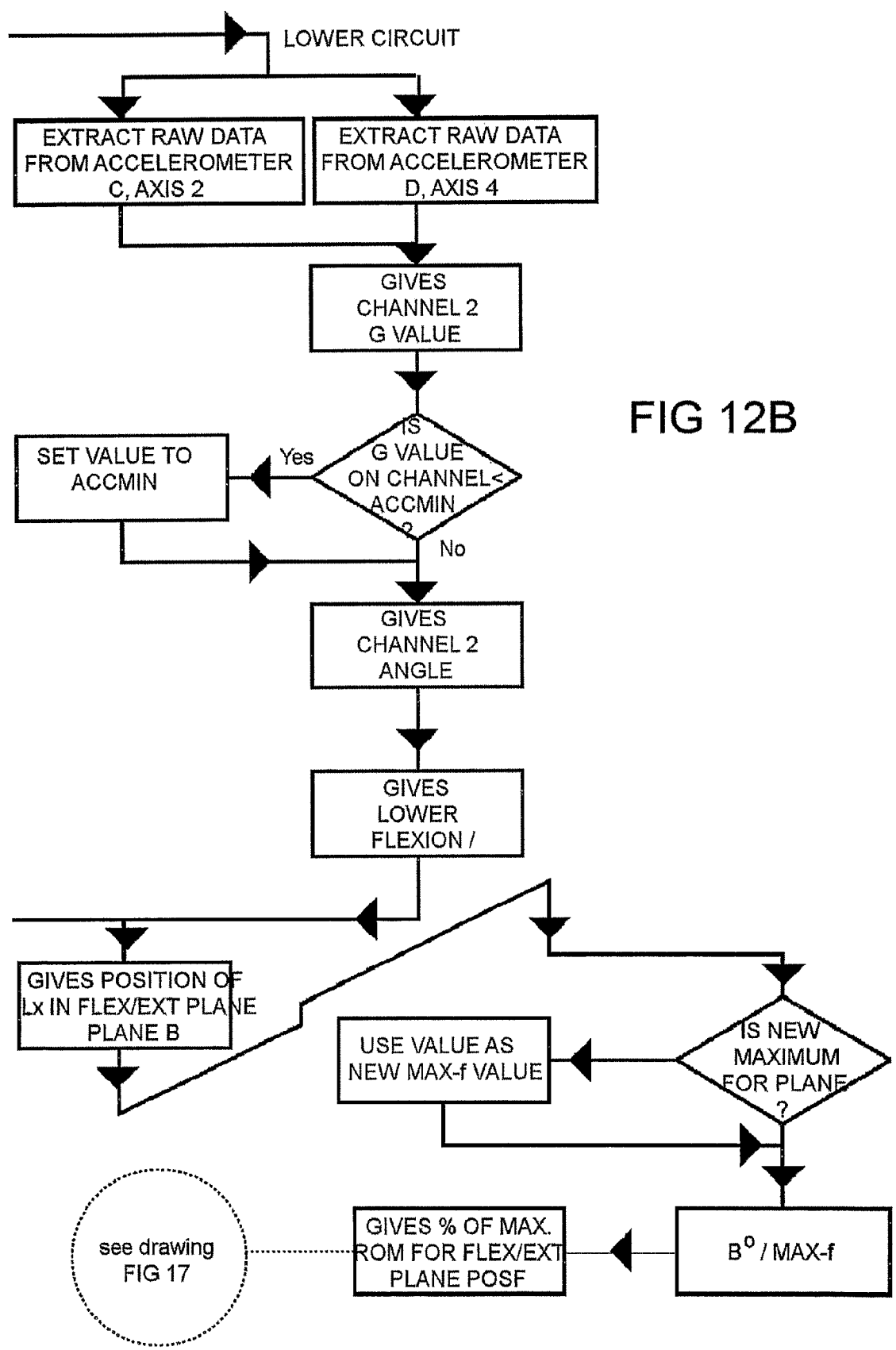

In FIG. 12
  $POS_{LF}=B°$
  MAX-f
  Where:
  $POS_F$=Position in the Flexion/Extension Plane
  B°=Relative Angle of the Lower Back in the Flexion/Extension Plane
  MAX-f=Maximum Range of Movement to date in the Flexion/Extension Plane
  $ACC_{MIN}$=Minimum usable value for accelerometer output.

Figure 13A:
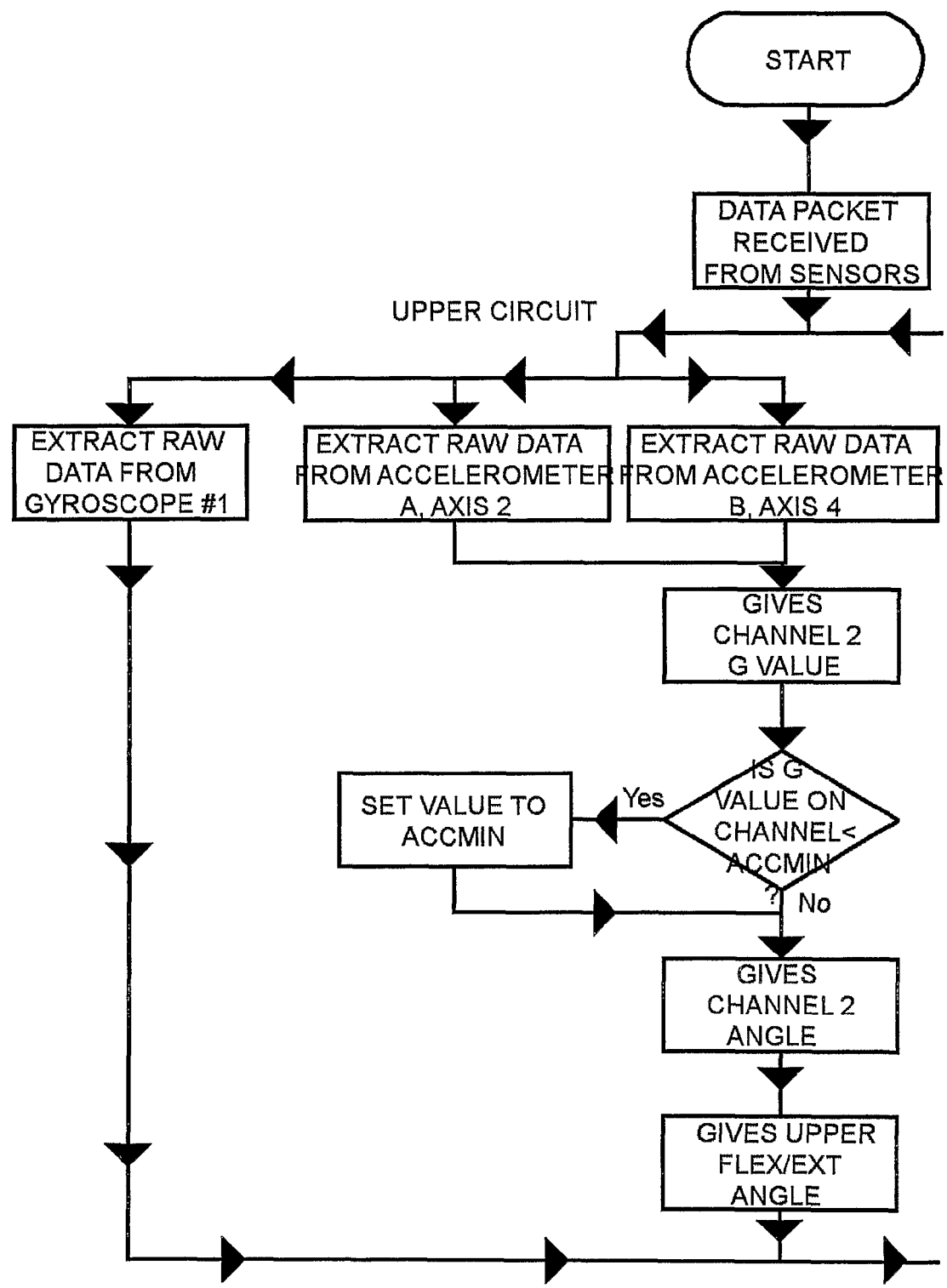
FIGS. 13a and 13b show a flow diagram of software for calculating rotation of a lower back.
Figure 13B:
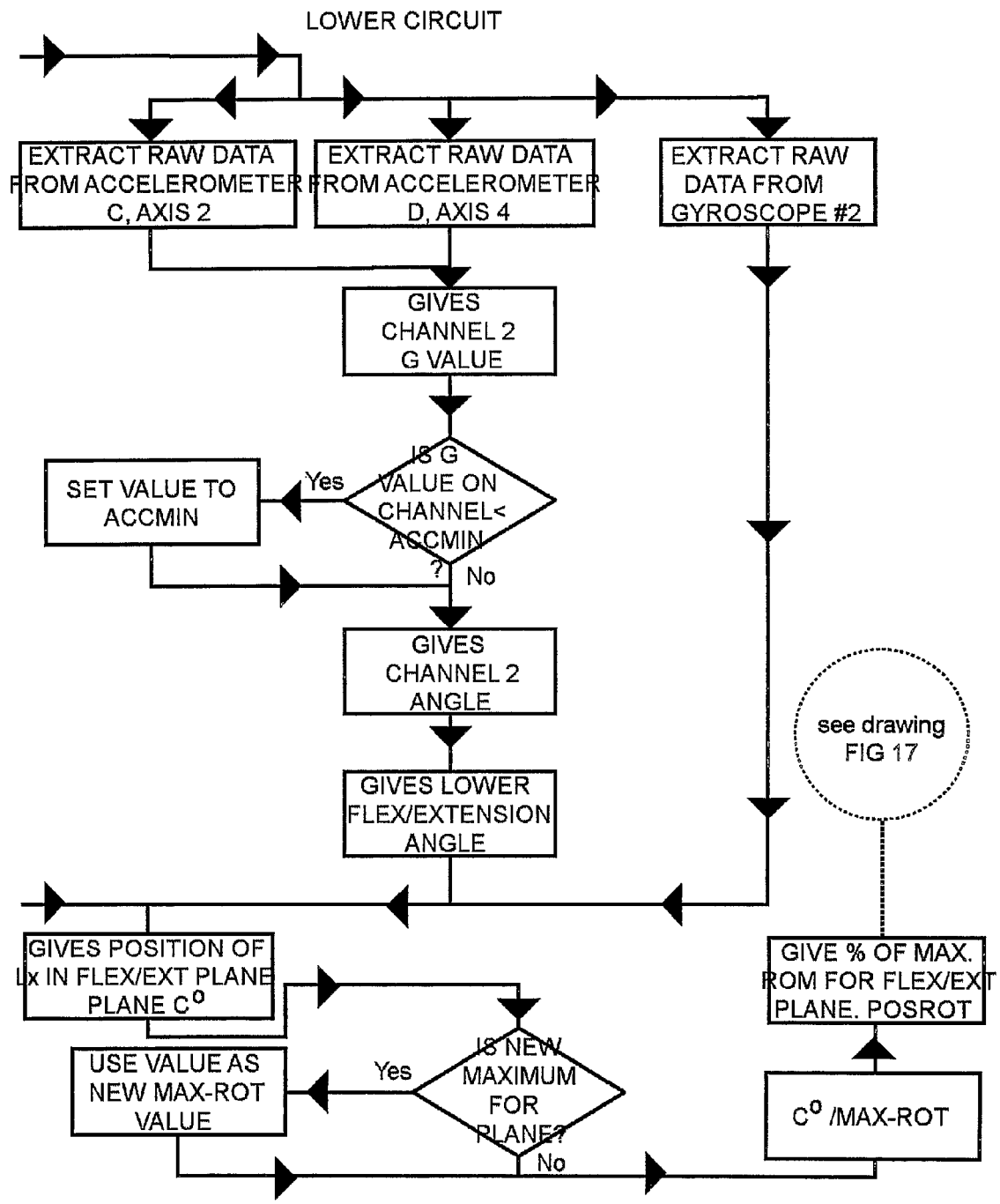

In FIG. 13
  $POS_{ROT}$=Position in the Flexion/Extension Plane
  C.°=Relative Angle of the Lower Back in the Flexion/Extension Plane
  $MAX_{ROT}$=Maximum Range of Movement to date in the Flexion/Extension Plane
  $ACC_{MIN}$=Minimum usable value for accelerometer output.

Figure 14A:
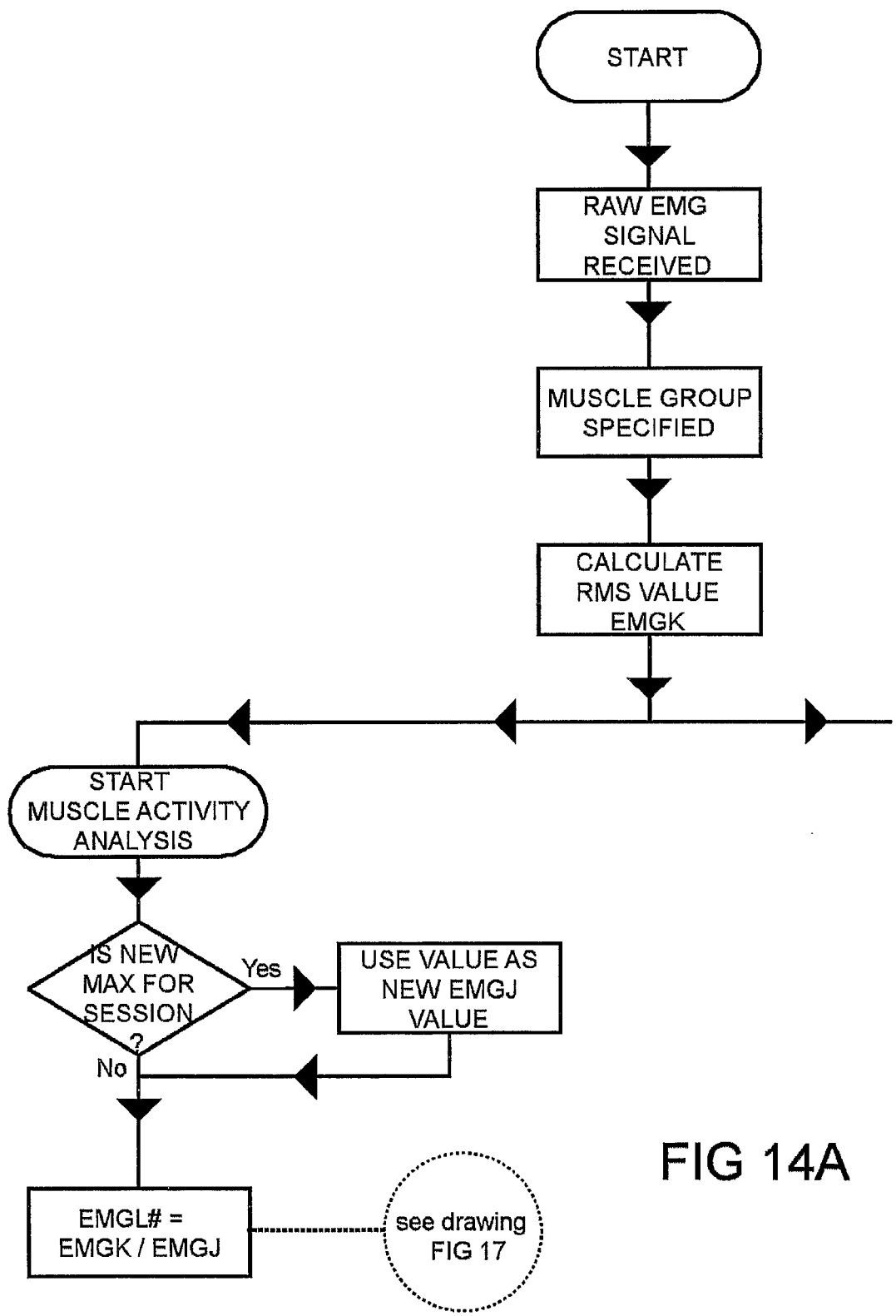
FIGS. 14a and 14b show a flow diagram of software for calculating EMG level and muscle fatigue.
Figure 14B:
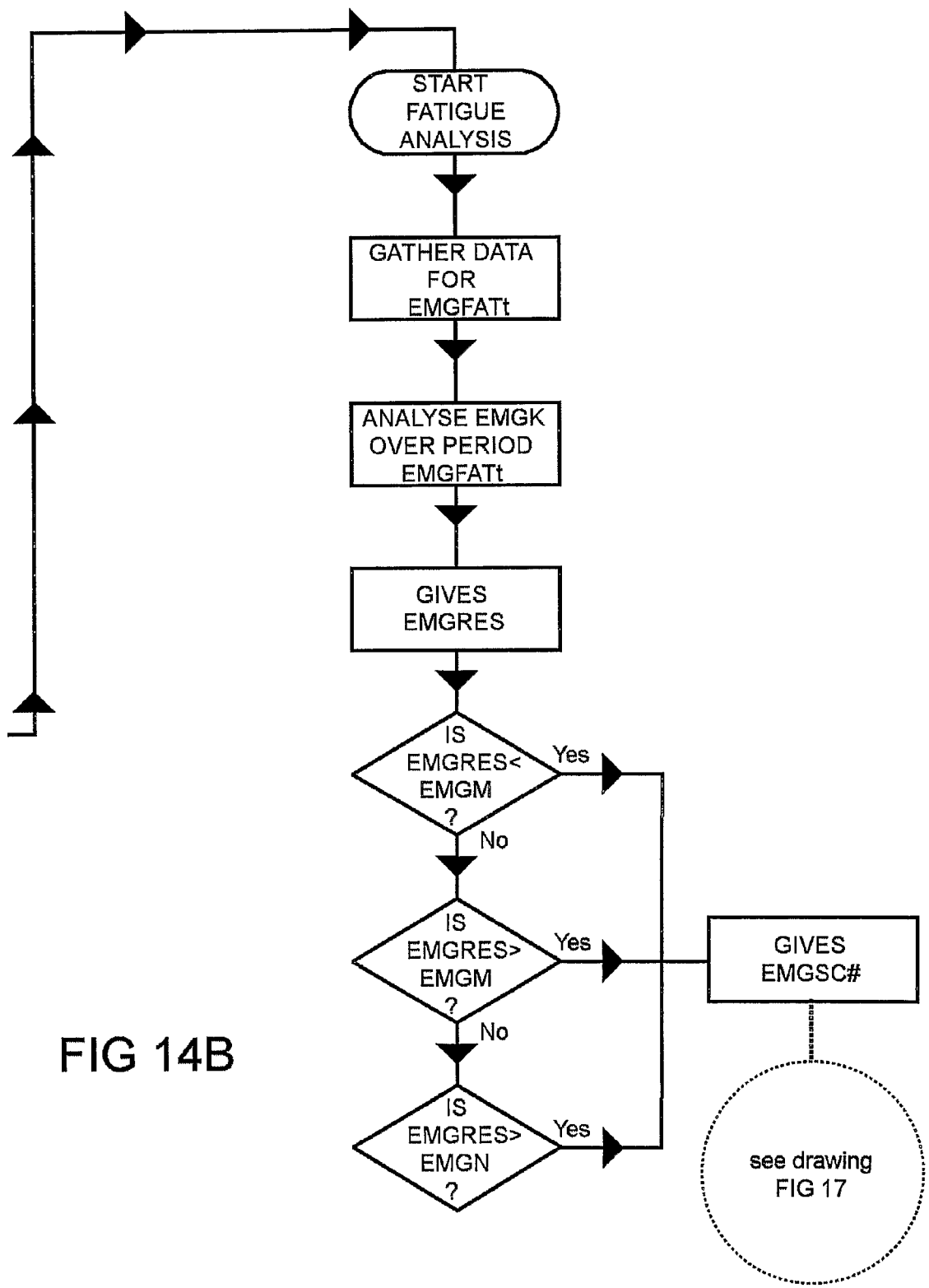

In FIG. 14
  $EMG_J$=Self Calibrating personal maximum reading for EMG.
  $EMG_k$=Root Mean Squared value of raw EMG signal.
  $EMG_L$=EMG normalised value. A percentage of $EMG_J$
  $EMG_{FAT}$=EMG Fatigue Score.
  EMGFATt $EMG_{FATt}$=Period of time used for Fatigue Analysis
  $EMG_M$=EMG Fatigue Level—low grade
  $EMG_N$=EMG Fatigue Level—high grade
  $EMG_{RES}$=Result of EMG Fatigue Analysis
  $EMG_{SC}$=EMG Score
  Note: This diagram is repeated for each muscle group being measured.

Figure 15A:
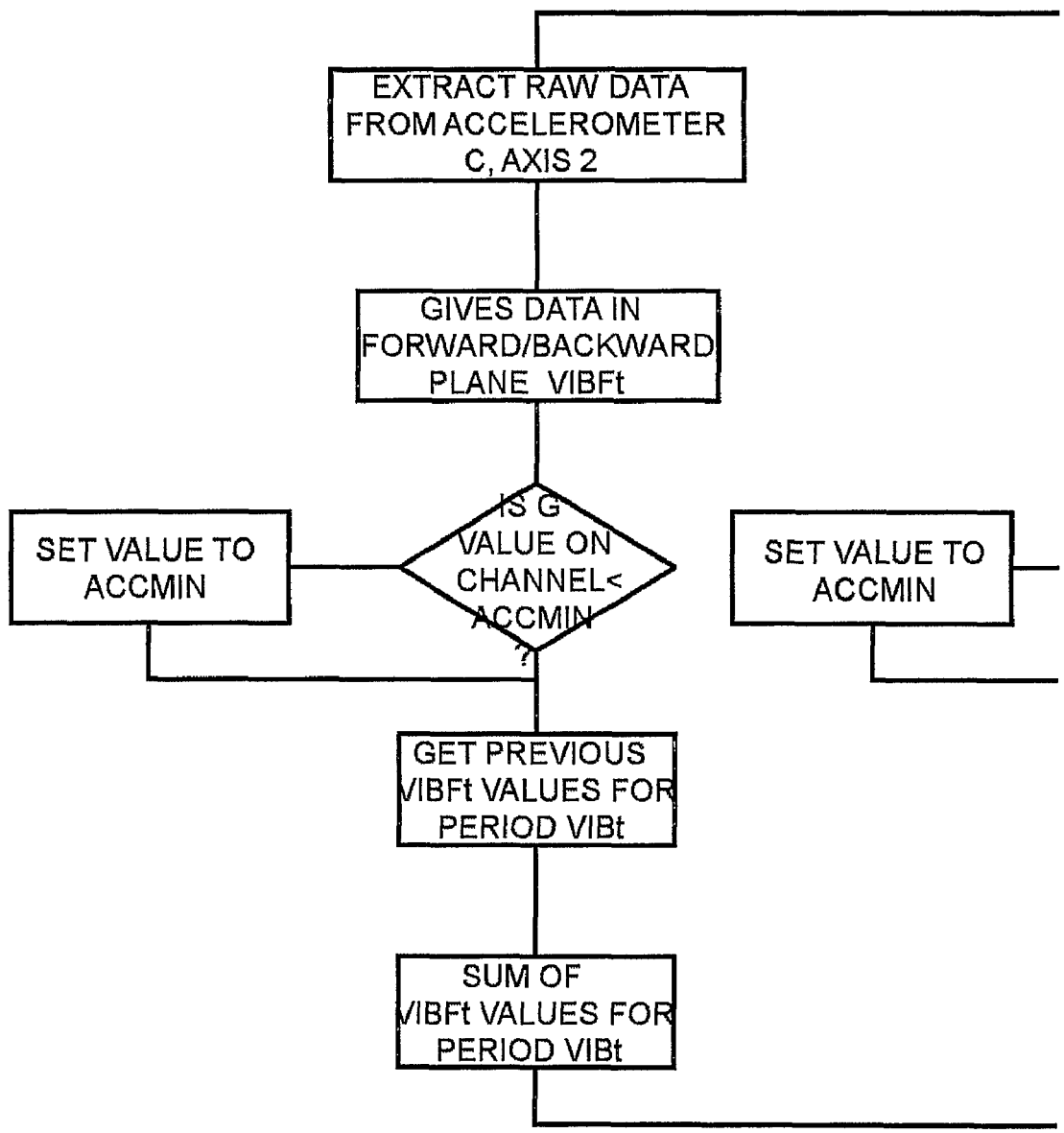
FIGS. 15a and 15b show a flow diagram of software for calculating vibration.
Figure 15B:
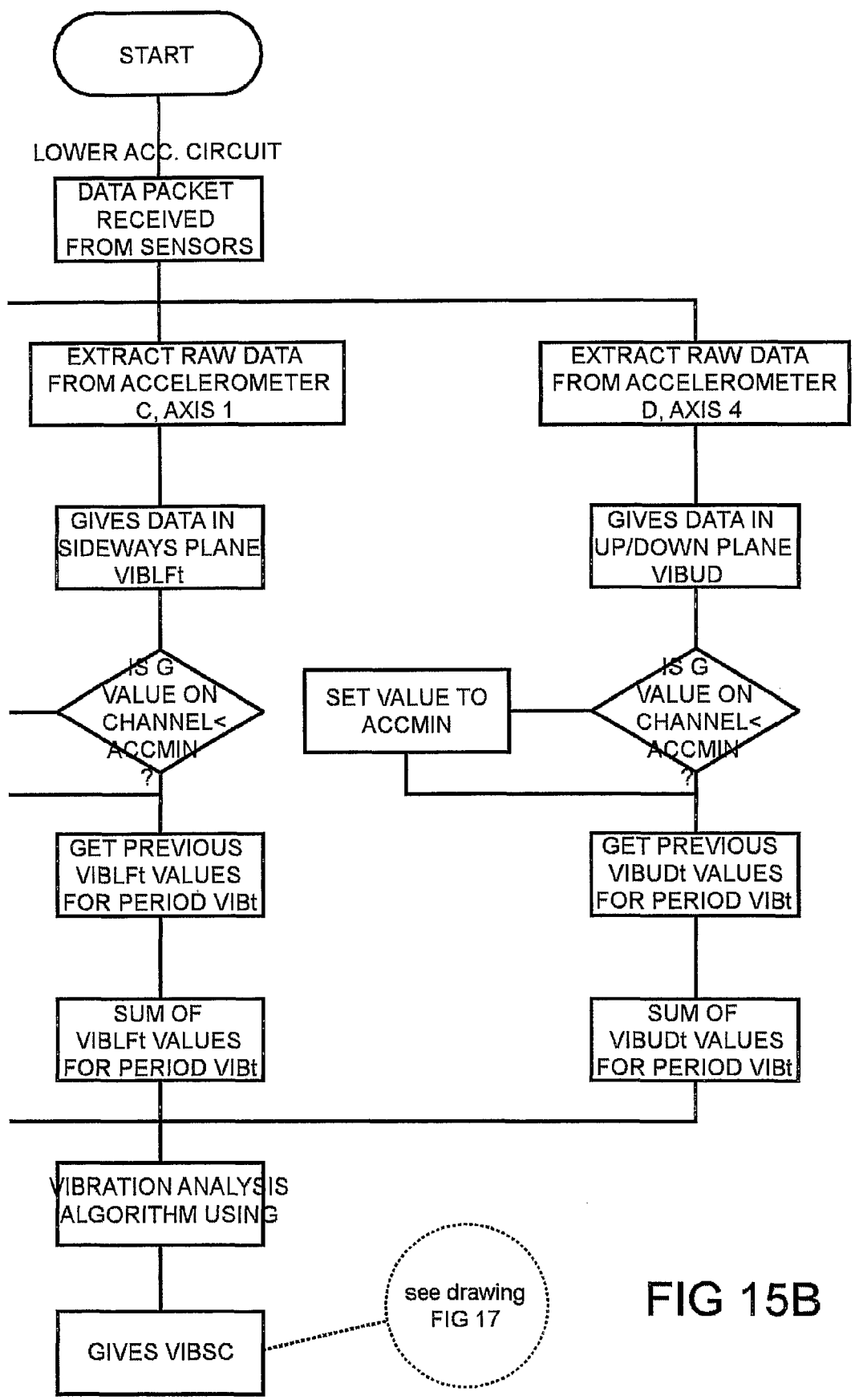

In FIG. 15
  $ACC_{MIN}$=Minimum usable value for accelerometer output
  $VIB_{LFt}$=Level of vibration for the lateral flexion plane at time t.
  $VIB_{Ft}$=Level of vibration for the flexion/extension plane at time t.
  $VIB_{UDt}$=Level of vibration for the vertical plane at time t.
  $VIB_{SC}$=Final result of the vibration analysis.
  $VIB_t$=Period of time used for vibration analysis.

Figure 16:
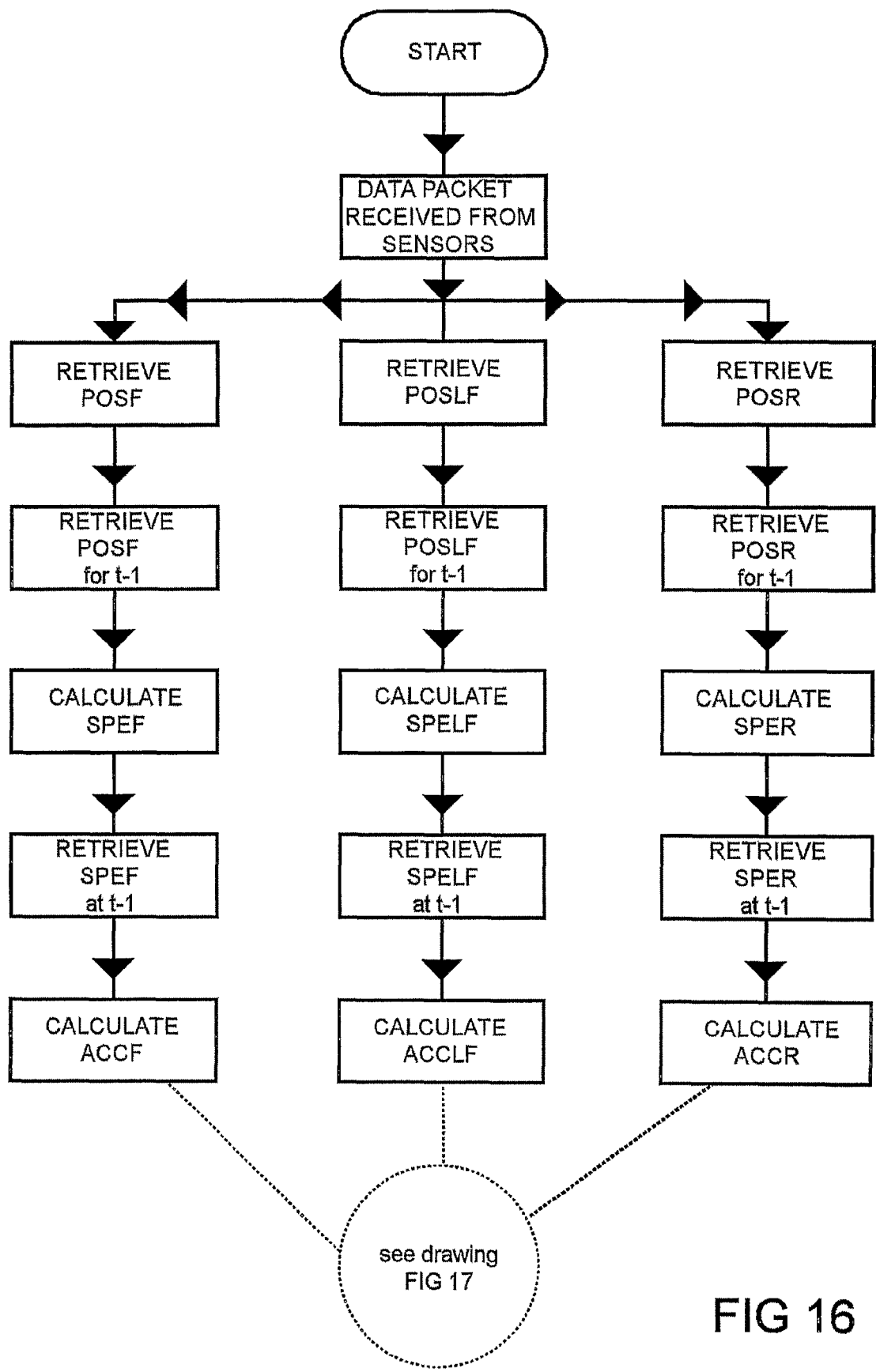
FIG. 16 shows a flow diagram of software for calculating velocity and acceleration.

In FIG. 16
  $POS_{LF}$=Position in Lateral Flexion Plane at time t.
  $POS_F$=Position in Flexion/Extension Plane at time t.
  $POS_{ROT}$=Position in Rotation Plane at time t.
  $POS_{ROT}$=Position in Rotation Plane at time t.
  $SPE_{LF}$=Speed in Lateral Flexion Plane.
  $SPE_F$=Speed in Flexion/Extension Plane.
  $SPE_{ROT}$=Speed in Rotation Plane
  $ACC_{LF}$=Acceleration in Lateral Flexion Plane.
  $ACC_F$=Acceleration in Flexion/Extension Plane.
  $ACC_{ROT}$=Acceleration in Rotation Plane.

Figure 17A:
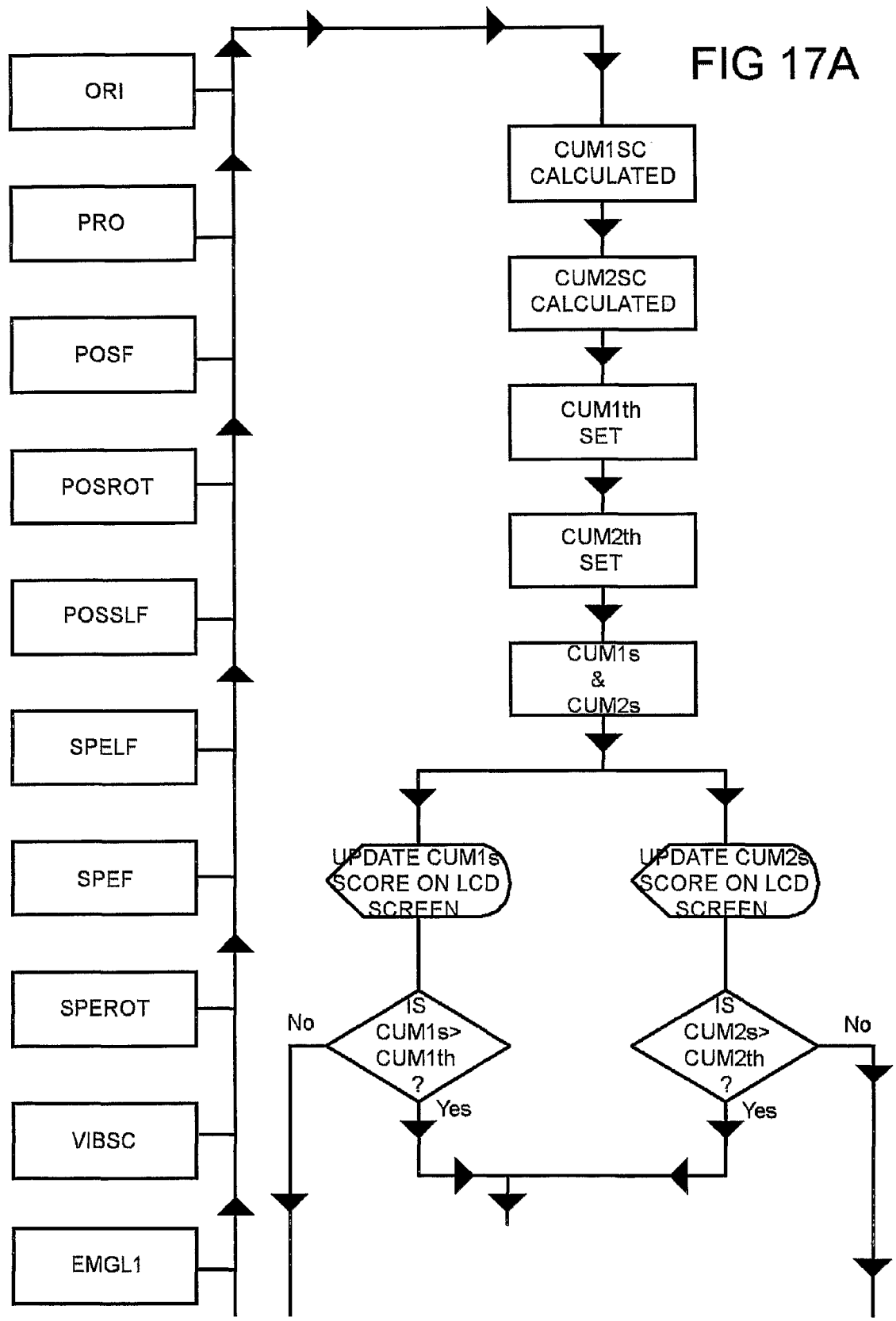
FIGS. 17a and 17b show a flow diagram of software for calculating cumulative risk of back injury.
Figure 17B:
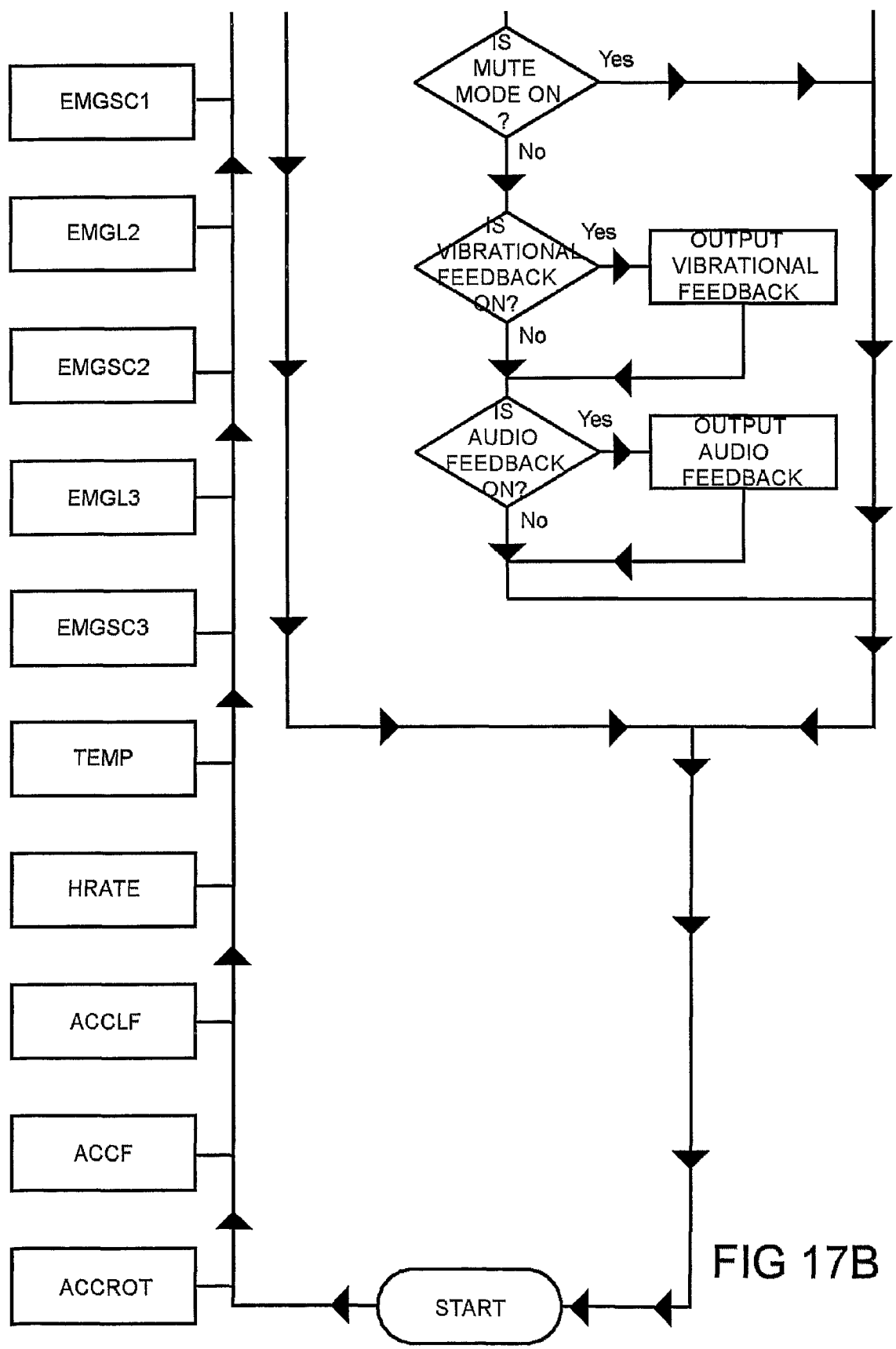

In FIG. 17
  t=period of time to which a data sample relates
  S=Sample Rate

CUM1*t*=Period of time in seconds of the 1st cumulative feedback window.

CUM1#=Number of data samples in the 1st cumulative feedback window. eg. for 5 minutes window at sample rate of 20 Hz.

CUM1#=6,000

CUM1*s*=Result of Data Scores for the period CUM1*t*

CUM1*th*=Threshold Score for the period CUM1*t*

CUM2*t*=Period of time in seconds of the $2^{nd}$ cumulative feedback window.

CUM2#=Number of data samples in the $1^{st}$ cumulative feedback window. eg. for 60 minutes window at sample rate of 20 Hz.

CUM2#=72,000

CUM2*s*=Result of Data scores for the period CUM2*t*

CUM2*th*=Threshold Score for the period CUM2*t*

PRO=Profile Data Result remainder as defined in previous documents

The software processes raw data received from the accelerometer, EMG and flexion circuits shown in FIGS. 6 to 8. The software also processes data from a Gyroscope circuit as well as profile data associated with the person being monitored. The profile data may allow calculation of parameters and risk thresholds to be tailored to personal habits and factors that may have a bearing on risk of back strain and/or injury such as age, sex, weight, height, family history, fitness level, occupation etc. Profile data may be obtained by means of a questionnaire or the like. A sample questionnaire for this purpose is set out in FIG. 18.

Finally, it is to be understood that various alterations, modifications and/or additions may be introduced into the constructions and arrangements of parts previously described without departing from the spirit or ambit of the invention.

The invention claimed is:

1. An apparatus for monitoring strain and/or load applied to a body of a vertebral mammal, said apparatus comprising:
    an acceleration sensor arranged for measuring acceleration of said body relative to an inertial frame of reference and for providing first data indicative of said acceleration, wherein said acceleration sensor includes at least one inertial sensor;
    a muscle sensing device arranged for measuring muscle activity and for providing second data indicative of said muscle activity;
    a non-transitory memory device coupled to the acceleration sensor and the muscle sensing device and arranged for storing said first and said second data; and
    a processor coupled to the acceleration sensor and arranged for processing said first and said second data to provide a measure of said strain and/or load applied to said body, wherein said processor is adapted to derive an angular displacement of the body from said first data.

2. The apparatus according to claim 1 wherein said processor is adapted to derive the angular displacement by calculating a forward tilt angle and a side tilt angle.

3. The apparatus according to claim 1, wherein the at least one inertial sensor includes an accelerometer.

4. The apparatus according to claim 3, wherein said accelerometer is adapted to measure acceleration along three orthogonal axes.

5. The apparatus according to claim 1, wherein the processor is configured to determine a displacement in a lateral flexion plane according to the first data.

6. The apparatus according to claim 1, wherein the processor is configured to determine a displacement in an extension flexion plane according to the first data.

7. The apparatus according to claim 1, wherein the processor is configured to use said first data and further data from a gyroscope to calculate a rotational position of said body.

8. The apparatus according to claim 1, wherein said muscle sensing device includes an electrode for measuring surface electromyography (EMG).

9. The apparatus according to claim 8, wherein said electrode is configured to be applied to a back of said mammal.

10. The apparatus according to claim 1, wherein each inertial sensor includes an analog to digital (A to D) converter for converting analog data to a digital domain.

11. The apparatus according to claim 10, wherein said A to D converter is configured to convert an analog output from the sensor to the first data prior to storing said first data.

12. The apparatus according to claim 1, wherein said processor is configured to execute an algorithm for evaluating risk of injury.

13. The apparatus according to claim 12, wherein said algorithm is adapted to cause the processor to evaluate said risk based on one or more risk components including profile data associated with said mammal.

14. The apparatus according to claim 13, wherein said profile data includes personal data and a family history.

15. The apparatus according to claim 1, further comprising a device for deriving a rotational position of said body.

16. The apparatus according to claim 15, wherein said device for deriving the rotational position includes a gyroscope.

17. The apparatus according to claim 1, wherein said processor is configured to calculate a body orientation according to the angular displacement.

18. The apparatus according to claim 1, wherein said body of said mammal includes a back, and the apparatus is applicable to monitor risk components associated with said strain and/or load applied to said back.

19. The apparatus according to claim 1, wherein said processor is configured to process the first data based on calibration constants.

20. A method of monitoring strain and/or load applied to a body of a vertebral mammal, said method comprising:
    using at least one inertial sensor to measure acceleration of said body relative to an inertial frame of reference and to provide first data indicative of said acceleration;
    using a muscle sensing device to measure muscle activity and to provide second data indicative of said muscle activity;
    storing said first and said second data in a non-transitory memory device; and
    processing said first and said second data by a processor to provide a measure of said strain and/or load applied to said body, wherein said processing includes deriving an angular displacement of the body from the first data.

21. The method according to claim 20, wherein said method is performed to monitor risk components associated with strain and/or load applied to a back of said mammal.

22. The method according to claim 20, wherein the at least one inertial sensor includes an accelerometer.

23. The method according to claim 22, wherein said acceleration is measured by said accelerometer along three orthogonal axes.

24. The method according to claim 20, further comprising calculating a displacement in a lateral flexion plane according to the first data.

25. The method according to claim 20, further comprising calculating a displacement in an extension flexion plane according to the first data.

26. The method according to claim 20, further comprising calculating rotation of said body according to the first data.

27. The method according to claim 20, wherein said step of measuring muscle activity includes measuring surface electromyography (EMG).

28. The method according to claim 27, wherein said EMG is measured at a back of said mammal.

29. The method according to claim 20, further comprising converting analog data from each inertial sensor to a digital domain, thereby obtaining the first data.

30. The method according to claim 29, wherein the converting of the analog data to the digital domain is performed prior to the storing said first data.

31. The method according to claim 20, wherein said processing is performed according to an algorithm for evaluating risk of injury.

32. The method according to claim 31, wherein said algorithm causes the processor to evaluate said risk based on one or more risk components including profile data associated with said mammal.

33. The method according to claim 32, wherein said profile data includes personal data and a family history.

34. The method according to claim 20, wherein said angular displacement is derived by calculating a forward tilt angle and a side tilt angle.

35. The method according to claim 20, further comprising deriving a rotational position of said body using said first data.

36. The method according to claim 35, wherein said rotational position is derived according to said first data and further data from a gyroscope.

37. The method according to claim 20, further comprising calculating a body orientation according to the angular displacement.

38. The method according to claim 20, wherein said processing includes applying calibration constants.

* * * * *